US010597632B2

(12) United States Patent
Alegria et al.

(10) Patent No.: US 10,597,632 B2
(45) Date of Patent: *Mar. 24, 2020

(54) **ANIMAL PRODUCT-FREE CULTURE MEDIUM FOR BACTERIA OF THE GENUS *CLOSTRIDIUM* AND A PROCESS FOR PRODUCING SUPERNATANT COMPRISING ONE OR MORE COLLAGENOLYTIC AND GELATINOLYTIC PROTEASES**

(71) Applicant: CRISTALIA PRODUTOS QUIMICOS FARMACEUTICOS LTDA., Itapira, SP (BR)

(72) Inventors: Marcos Castanheira Alegria, Itapira (BR); Lucidio Cristovao Fardelone, Itapira (BR); Marina Baiochi Riboldi Delalana, Itapira (BR); Josef Ernst Thiemann, Itapira (BR); Spartaco Astolfi Filho, Itapira (BR); Roberto Carlos Debom Moreira, Itapira (BR); Ogari de Castro Pacheco, Itapira (BR)

(73) Assignee: CRISTALIA PRODUTOS QUIMICOS FARMACEUTICOS LTDA., Itapira, SP (BR)

( * ) Notice: Subject to any disclaimer, the term of this patent is extended or adjusted under 35 U.S.C. 154(b) by 15 days.

This patent is subject to a terminal disclaimer.

(21) Appl. No.: 15/650,826

(22) Filed: Jul. 14, 2017

(65) Prior Publication Data
US 2018/0187144 A1    Jul. 5, 2018

Related U.S. Application Data

(63) Continuation of application No. 14/404,155, filed as application No. PCT/BR2013/000192 on May 29, 2013, now Pat. No. 9,725,692.

(30) Foreign Application Priority Data

May 31, 2012    (BR) .......................... 1020120131102

(51) Int. Cl.
*C12N 1/20*    (2006.01)
*A61K 38/48*   (2006.01)
(Continued)

(52) U.S. Cl.
CPC ............ *C12N 1/20* (2013.01); *A61K 38/4886* (2013.01); *C12N 9/52* (2013.01); *C12P 1/04* (2013.01); *C12Y 304/24003* (2013.01)

(58) Field of Classification Search
None
See application file for complete search history.

(56) References Cited

U.S. PATENT DOCUMENTS 7,560,251 B2 *   7/2009  Wang ..................... C07K 14/33
                                                424/236.1
2010/0086971 A1  4/2010  Suppmann et al.

FOREIGN PATENT DOCUMENTS

EP    2133415 A1    12/2009
WO    9824889 A1    6/1998
(Continued)

OTHER PUBLICATIONS

Solabia, http://www.solabia.com/solabia/content/NT0000440A.pdf, published Jun. 30, 2008, accessed Apr. 12, 2016.*
(Continued)

*Primary Examiner* — Erin M. Bowers
(74) *Attorney, Agent, or Firm* — Roberts Calderon Safran & Cole, P.C.

(57) ABSTRACT

The present invention refers to a culture medium and a process for producing proteases with collagenolytic and gelatinolytic activity by bacteria of the genus *Clostridium*. Particularly, the present invention refers to an animal prod-
(Continued)

uct-free culture medium for *C. histolyticum*, characterized by comprising non-animal origin peptones, preferably vegetable peptones, yeast extract and the amino acids cysteine and arginine. The present invention also refers to a process for producing *Clostridium histolyticum* liquid culture supernatant comprising one or more proteases with collagenolytic and gelatinolytic activity, and pharmaceutical composition comprising as active ingredient the supernatant or the supernatant optionality purified.

12 Claims, 14 Drawing Sheets

(51) Int. Cl.
    *C12P 1/04*      (2006.01)
    *C12N 9/52*      (2006.01)

(56) References Cited

FOREIGN PATENT DOCUMENTS

| | | |
|---|---|---|
| WO | 9854296 A1 | 12/1998 |
| WO | 2001005997 A2 | 1/2001 |
| WO | 2005035749 A2 | 4/2005 |
| WO | 2007089851 A2 | 8/2007 |
| WO | 2012125948 A1 | 9/2012 |

OTHER PUBLICATIONS

Rolfe et al., Infect. Imm. 25(1): 191-201 (1979).*
Macek et al., J. Am. Pharm. Ass'n. 39(7): 365-369 (1950).*
Solabia, http://www.solabia.com/content/NT0000440A.pdf, published Jun. 30, 2008, Apr. 12, 2016.
Fang et al., "Production of Clostridium difficile toxin in a medium totally free of both animal and dairy proteins or digests" PNAS, vol. 106, No. 32, 2009, pp. 13225-13229.
Bond et al., "Purification and Separation of Individual Collagenases of Clostridium histolyticum Using Red Dye Ligand Chromatography", Biochemistry, vol. 23 pp. 3077-3085, 1984.
MaClennan et al., "Bacterial Digestion of Collagen", J. Clin. Invest., vol. 32 pp. 1317-1322, 1953.
Bergman et al., "Factors Affecting the Elaboration by Clostridium Histolyticum of Proteinases Capable of DebridingThird Degree Bum Eschars on Guinea Pigs:", Journal of Bacteriology, vol. 82 pp. 582-588, 1961.
Mead, "The Amino Acid-fermenting Clostridia", J. Gen. Microbiol., vol. 67, pp. 47-56, 1971.
Busta et al., "Effects of Soy Proteins on the Growth of Clostridium Perfringens", Appl. Microbiol, vol. 22 No. 2 pp. 177-183.
Demain et al., "Tetanus Toxin Production in Soy-Based Medium: Nutritional Studies and Scale-up into Small Fermentors", Letters in Applied Microbiology, No. 45, pp. 635-638, 2007.
Bond et al., "Characterization of the Individual Collagenases from Clostridium histolyticum", Biochemistry, vol. 23 pp. 3085-3091.
Moore et al., "Photometric Ninhydrin Method for Use in the Chromatography of Amino Acids", the Journal of Biological Chemistry, vol. 176, pp. 367-388, 1948.

* cited by examiner

*Diluted samples 4X

ANIMAL PRODUCT-FREE CULTURE MEDIUM FOR BACTERIA OF THE GENUS *CLOSTRIDIUM* AND A PROCESS FOR PRODUCING SUPERNATANT COMPRISING ONE OR MORE COLLAGENOLYTIC AND GELATINOLYTIC PROTEASES

FIELD OF APPLICATION

The present invention is related to the field of microbiology and biotechnology. Particularly, this invention is related to an animal product-free culture medium and a process for producing a supernatant of *Clostridium* liquid culture comprising one or more collagenolytic and gelatinolytic proteases.

BACKGROUND OF THE INVENTION

Collagenase (clostridiopeptidase A, EC 3.4.24.3) is a proteolytic enzyme that hydrolyzes collagen proteins, both in their native and denatured (gelatins) form. No other enzyme is capable of cleaving native collagen, due to its distinct amino acid composition (presence of a numerous amount of imino acids, represented by tripeptide Gly-Pro-X, where X is, frequently, proline or hydroxyproline), and macrostructure (complex triple-helix structure).

Collagenase, isolated or as the main component of compositions comprising other proteolytic enzymes, has been widely used since the 70's in the treatment of several diseases and pathological conditions. All diseases and conditions in which collagenase is administered are associated with the excessive deposit of collagen and the erratic accumulation of fibrous tissue rich in collagen. Such diseases and conditions are denominated collagen-mediated diseases, and the local application of compositions containing collagenase is one of the possible alternative treatments to surgical intervention. The use of collagenase compositions for the treatment of necrotic tissue debridement (burns, skin lesions, etc.) has also been approved by regulatory agencies, showing surprising results on improving scarification processes.

Some therapeutic applications of collagenase compositions are: burn treatment, with a concomitant beneficial effect over tissue regeneration; enzymatic debridement of wounds and treatment of infected wounds and ulcers (skin and decubitus ulcers); herniated intervertebral disc disease treatment; selective lysis of collagen fibers of the eye's vitreous body; Dupuytren's disease treatment; Peyronie's disease treatment; adhesive capsulitis treatment; lateral epicondylitis treatment, Carpal Tunnel Syndrome and plantar fasciitis; regeneration of damaged nerves; also being widely used in medical specialties such as plastic surgery and in several dermatological and aesthetic procedures, for example, in the treatment of cellulites and scars, such as acne, keloid and other hypertrophic scars through intralesional injection of purified collagenase.

Other studies have shown the use of collagenase compositions in rheumatoid arthritis, metastasis, angiogenesis and cirrhosis.

Collagenases have also been described as important tools in specific organ transplantation i.e. isolation of pancreatic islets of Langerhans, microvascular endothelial cells, hepatocytes and chondrocytes (WO9824889). Tissue dissociation mediated by collagenolytic enzymes is a critical step in several cell isolation procedures.

The collagenases used in the majority of the therapeutic applications described above are obtained from supernatant, purified or not, of bacterial cultures, most specifically of *Clostridium histolyticum* cultures. *Clostridium histolyticum* is an anaerobic, gram-positive and spore-forming cylindrical bacterium. The collagenolytic activity of the extracellular enzymes of such bacteria has been known for over 50 years, when it was isolated for the first time an extracellular enzyme capable of digesting cattle Achilles tendons.

Currently, it is of common knowledge that several microorganism species when cultured in specific conditions are capable of producing collagenase. However, *Clostridium* sp, most specifically *Clostridium histolyticum*, is still the main source of collagenolytic and gelatinolytic enzymes for therapeutic application due to its higher enzymatic productivity and activity against several collagen forms and its peptides.

Other collagenase sources for therapeutic use include mammal cells, crustaceans (crabs, shrimp), fungi and other bacteria (*Streptomyces, Pseudomonas* and *Vibrio*).

The ability of *Clostridium* collagenases to digest several kinds of collagen (type I, II, III, VII and X) and gelatin is the major factor that differentiates these proteases from other collagenase sources. Aforesaid clostridial enzymes not only present higher collagenolytic activity when compared to vertebrate collagenases but it also presents an optimum pH for its activity within human physiological pH range.

Studies from late 1950s to mid-1980s showed the existence of several types of *C. histolyticum* collagenases and characterized their specificity and stability gradually. Bond and Van Wart (1984; Biochemistry, 23: 3077-3085) isolated six different enzymes from commercial collagenase preparations with molecular weights varying from 68 kDa to 130 kDa and isoelectric points between pH 5.5 and 6.5; further, classifying them in two classes according to substrates specificity. Class I—higher activity against high molecular weight collagens (native collagen: intact); Class II—preference for low molecular weight collagen fragments (denatured collagen: gelatins). These activities seem to be complementary, and there is evidence of its synergistic action on native collagen.

In addition to the several classes I and II collagenase isoforms, conventional preparations of collagenase, based on the supernatant of *Clostridium histolyticum* cultures, contain over 30 different enzymes. The primary constituent of the culture supernatant are the collagenases (classes I and II), however, other important proteases are also present, such as: neutral proteases i.e.: gelatinases, clostripains (clostridiopeptidase B, EC 3.4.22.8), trypsins, elastases and aminopeptidases. Non-proteolytic enzymes including: galactosidase, acetylglucosaminidase, fucosidase, phospholipase, neuraminidase (or sialidase) and hyaluronidase can also be found. Of the aforementioned proteolytic and non-proteolytic enzymes, sialidase, hyaluronidase and collagenase are deeply involved in the degradation process of extracellular matrix. The presence of this "enzymatic combination" is required to obtain compositions suitable to be used as enzymatic debridement agent for skin lesion and organ transplant (i.e. isolation of pancreatic islets).

Furthermore, either purified or recombinant, collagenase alone is inefficient in tissue dissociation due to incomplete hydrolysis of collagen polypeptides and to its limited activity when high concentrations of non-collagen proteins and other macromolecules are found in the extracellular matrix. For such reason, the most used collagenase composition for tissue dissociation and debridement is a crude or partially purified preparation (obtained by few purification steps), since the presence of enzymes which act on native collagen and reticular fibers in addition to enzymes responsible for the hydrolysis of other proteins, polysaccharides and lipids in the extracellular matrix of connective and epithelial tissue are required. The complex composition of crude collagenase preparations brings consequences to the production process, due to difficulties to define expression patterns of the proteolytic enzymes of the final composition.

On the other hand, the use of collagenase compositions for the treatment of collagen-mediated diseases require high purity of the preparations, due to the need of a specific action on digestion of collagen; such treatments are administered through local injections. In these cases, the purification processes of collagenase from the supernatant of *C. histolyticum* cultures are complex, including numerous steps with different strategies of purification.

In general, the purity of collagenase composition is directly related to the therapeutic application intent. However, regardless of the therapeutic application, a defined process for culturing *Clostridium histolyticum* is essential to direct the production in order to obtain the proteases of interest in the supernatant, purified or not.

The enzymatic activity and the concentration of proteases in *C. histolyticum* cultures supernatant vary according to the bacterial strain, culture medium, culture conditions, culture age, cellular density, among other variables. The intrinsic variability of this type of biotechnological process implies in exhaustive quality control analysis of the batches, increasing production costs. Moreover, the loss of efficacy of traditional collagenase over storage, regardless of the storage conditions, is strongly related to the enzymatic composition of the culture supernatant. For such reason, defined culture conditions which direct the production of the desired collagenolytic and gelatinolytic enzymes, in special collagenases, are required.

It is well known that the production of extracellular proteases by microorganisms is strongly influenced by components of the culture medium, especially by carbon and nitrogen sources, and physical factors such as, for instance, pH, temperature, inoculum volume, rate of orbital agitation and incubation time. There is no pre-defined culture media for specific proteases production; each microorganism has its own physicochemical and nutritional idiosyncratic requirements for growth and enzymatic secretion.

Proteins and peptides are the main source of carbon and nitrogen in *Clostridium* culture, being required for protein expression as well as growth. Therefore, brain-heart infusion (BHI), tryptose, peptone proteose, meat extract, casein and gelatin are commonly found in *C. histolyticum* culture medium. Not only, inorganic salts, vitamins, glucose, yeast extract, sodium thioglycolate and ferrous sulphate are also found in different concentrations in such culture media.

Since 1930's, several authors stated that animal derived peptones are essential for *C. histolyticum* growth and enzymatic production.

Later, in the 1950s, MacLennan et al. (1953; J. Clin. Invest., 32: 1317) evaluated how several carbon and nitrogen sources (phytones, peptones, collagen and it's derivatives, and glucose), as well as vitamin and inorganic salts concentration, pH and $Fe^{++}$ influence *C. histolyticum* growth and collagenolytic and gelatinolytic enzyme expression (several strains). Ferrous salt and animal derived peptone were defined as crucial for maximum enzymatic yield. The results presented in this study have been considered to determine the "conventional culture medium" for *C. histolyticum* collagenase production for several decades.

Commonly described as examples of animal derived peptones are: bacto-peptone, peptone proteose, hydrolyzed casein, casein tryptic hydrolysate, among others. Combinations of these components with vegetable peptones have also been described. For example, Bergman et al. (1961; Journal of Bacteriology, 82: 5829) obtained good results culturing *C. histolyticum* in a culture medium which contains peptone proteose, casein hydrolysate, soy tryptic hydrolysates and vitamins. The authors also demonstrated that, in the absence of inorganic salts, the collagenase productivity is equal to or greater than the one presented by MacLennan et al. (1953), however, with a decrease in the production of azocaseins, which is an interesting fact, since it facilitates later purification procedures (called PTV culture medium).

Besides the importance of animal derived peptones for the growth and enzymatic production in cultures of *C. histolyticum*, the influence of other components in the culture medium has also been investigated in order to define metabolic patterns for this species, thus improving culturing conditions.

Mead (1971; J. Gen. Microbiol., 67: 47) describes the pattern of amino acids intake in several *Clostridium* species during its growth, classifying them into groups according to their nutritional needs. In the aforementioned study, *Clostridium histolyticum* is considered capable of fermenting amino acids, and is sub-classified in the so called Group II (*C. botulinum; C. histolyticum; C. cochlearium; C. subterminale*). Even though serine, glutamine, glycine and valine are the main amino acids used by these species, their addition in culture medium produces no or little effect on the bacterial growth. However, substitution of partial casein hydrolysate by casamino acids significantly increases the observed bacterial growth rate (culture medium used: vitamins, inorganic salts, tryptophan, cysteine hydrochloride, casamino acids—2 g/L or casein hydrolysate—3% w/v and meat extract). Unfortunately, the author did not analyze the protease production.

More frequent than the amino acids intake, glucose intake as energy source for several microorganisms has been well documented. Particularly, for *C. histolyticum* the addition of glucose (and other sugars) has been correlated with a decrease in bacterial growth rate (Mead, 1971). Thus despite being initially classified as saccharolytic species, due to their ability to metabolize carbohydrates as energy source, several strains of *C. histolyticum* are inefficient fermenters of simple sugars such as glucose, maltose, among others. Moreover, a decrease in growth rate is even more prominent when culturing *C. histolyticum* under aerobic conditions in media containing glucose, suggesting the existence of two inhibiting factors: sugars and oxygen/air.

Not only does glucose negatively influence bacterial growth, it has also been reported that glucose containing media decrease protease expression in *Clostridium* cultures (*C. difficile*, for example). This observation suggests that there is a relationship between repression of toxin expression and the composition of culture medium with rapidly consumable carbon sources.

As discussed previously, *Clostridium* bacterial growth rate and protein expression are affected by nutritional requirements as well as the maintenance of an anaerobic environment. *C. histolyticum* tolerates few amounts of oxygen, as observed to other anaerobes and also other species of the genus, being considered an aerotolerant microorganism. Despite this, minimal conditions of anaerobiosis must be assured for growth and production of collagenolytic and gelatinolytic protease by *C. histolyticum* liquid cultures.

Additionally, reducing agents are also considered critical in anaerobic liquid culture. Among the most frequently used agents are: meat digest, glucose, sodium thioglycolate, cysteine, iron salts, metallic iron or a mixture of both.

To this date, it remains unknown which culture medium ingredients influence *C. histolyticum* growth and protease secretion. There is a consensus only about the importance of animal source ingredients, particularly peptones, to *Clostridium histolyticum* growth and protease expression, i.e. collagenases.

The conventional *C. histolyticum* culturing processes present several disadvantages, such as: low yield, low reproducibility and incomplete separation of impurities. Furthermore, one of the major drawbacks of such culture processes is the predominant use of animal derived components to obtain collagenolytic and gelatinolytic proteases for therapeutic use in humans.

The presence of animal derived components in such culture processes offers additional and undesirable potential risk of infections and anaphylactic reactions. A well-known example of disease caused due to interspecific horizontal transmission of pathogens is the bovine spongiform encephalopathy (prion disease; "Mad Cow disease"). Its transmission from the original host (bovine) to man was first recorded in 1993, due to contact with infected physiological fluids and consumption of infected animal meat.

In the last decade, regulatory agencies have been encouraging the pharmaceutical industry to use bacterial culture media comprising only non-animal derived components. However, care must be taken when considering non-animal derived components since these are often processed using animal derived enzymes. Even being a very small fraction of the final culture media, the presence of animal derived enzymes prevents media classification as animal product-free.

The following patents and papers state different animal product-free culture media for *Clostridium*: WO9854296 (1998, Chiron), WO0105997 (2000, Massachusetts Institute of Technology), WO2005035749 (2004, Allergan), Busta & Schroder (1971, Effect of soy proteins on the growth of *Clostridium perfringens*. *Appl. Microbiol*, 22(2), 177-183; Demain et al. (2007, Tetanus toxin production in soy-based medium: nutritional studies and scale-up into small fermentors. *Lett. Appl. Microbiol.*, 45(6), 635-638); Fang et al. (2009, Production of *Clostridium difficile* toxin in a medium totally free of both animal and dairy proteins or digests. PNAS, vol. 106: 13225-13229).

Usually, soy based and yeast extracts components are able to sustain growth rate as well as protease expression and secretion when used to replace animal derived peptones in the culture media of some *Clostridium* species such as, *C. sporogenes, C. tetanus, C. botulinicum*.

However, particularly to *C. histolyticum*, there is no animal product-free culture media that stimulate the production of collagenolytic and gelatinolytic proteases in a way at least equivalent to the conventional animal derived media.

The culture media described so far to *C. histolyticum* present disadvantages such as: presence of animal derived components, high cost associated with its complex composition, low collagenase expression and long culturing periods required to obtain a supernatant with collagenolytic and gelatinolytic activity appropriate for industrial production with therapeutic purposes.

Attempts for obtaining an animal product-free culture medium that would be appropriate for *C. histolyticum* growth and collagenase production are reported below.

The document WO2007089851 (2007; Auxilium) describes *C. histolyticum* culture conditions in order to obtain collagenases. Although it describes the production of collagenases by *C. histolyticum* in an animal product-free culture medium, it still emphasizes that in order to produce collagenases with higher reproducibility, a culture medium comprising animal derived peptone is preferred. Only the animal derived culture medium was capable of producing the collagenases in adequate proportion to maximize its synergistic activity, resulting in a therapeutic benefit. Other than peptones (vegetable and/or animal), the culture medium described above may contain amino acids (glutamine, tryptophan and asparagine), yeast extract, inorganic salts, glucose and vitamins.

The document US20100086971 (2009; Roche) describes a culture medium for *C. histolyticum* which includes vegetable derived peptone. However, in the US2010008671 document, an animal derived additive—fish gelatin—is considered crucial to the higher collagenolytic activity observed in these culture supernatants. It is emphasized that only the liquid composition containing vegetable peptone with fish gelatin can support greater bacterial growth and collagenolytic activity when compared to the standard culture medium comprising animal derived peptone.

Thus, until the present moment, no culture medium completely free from animal derived components has been able to support an adequate industrial production of *C. histolyticum* collagenases as demonstrated to conventional culture media containing animal peptones.

For such reason, there is a clear need for developing animal product-free culture media as well as processes for production of *C. histolyticum* collagenolytic and gelatinolytic proteases.

Therefore, the present invention provides an animal product-free culture medium for bacteria of the genus *Clostridium*, preferably *C. histolyticum*, and an industrially adequate process for producing a supernatant comprising one or more collagenolytic and gelatinolytic proteases, in particular collagenases, for therapeutic purposes.

SUMMARIZED DESCRIPTION OF THE INVENTION

The present invention refers to an animal product-free culture medium for *Clostridium* comprising water, non-animal derived peptone or its derivatives, yeast extract and the amino acids cysteine and arginine, or pharmaceutically acceptable salts thereof. Preferably, the *Clostridium* is a *Clostridium histolyticum* strain.

The culture medium of the present invention further comprises one or more additives selected from the group consisting of agent for pH adjustment within the range of 7 to 8, reducing agent, inorganic salts and vitamins.

The non-animal derived peptone may be vegetable or yeast peptone. Preferably, the non-animal derived peptone is a vegetable peptone selected from the group consisting of soy, cotton, wheat, sunflower, rice, peanut, fava bean, peas, potato, corn and mixtures thereof. Most preferably, the vegetable peptone is a soy peptone.

The culture medium of the present invention comprises non-animal derived peptone at a concentration range from 0.5% to 5% w/v, yeast extract at a concentration range from 0.5% to 5% w/v, cysteine, or its pharmaceutically acceptable salts, at a concentration range from 0.01% to 0.1% w/v, and arginine, or its pharmaceutically acceptable salts, at a concentration range from 0.1% to 1% w/v. Preferably, the non-animal derived peptone is at a concentration range from 1% to 4% w/v, yeast extract is at a concentration range from 1% to 4% w/v, cysteine, or its pharmaceutically acceptable salts, is at a concentration range from 0.03% to 0.07% w/v; and arginine, or its pharmaceutically acceptable salts, is at a concentration range from 0.25% to 0.7% w/v. Most preferably, the non-animal derived peptone is at a concentration of 3% w/v; yeast extract is at a concentration of 3% w/v;

cysteine, or its pharmaceutically acceptable salts, is at a concentration of 0.0625% w/v; and arginine, or its pharmaceutically acceptable salts, is at a concentration of 0.375% w/v.

Contrary to the culture media conventionally used for *C. histolyticum* growth comprising at least one animal derived ingredient, the culture medium of the present invention is animal product-free and, surprisingly, stimulate a higher expression of collagenolytic and gelatinolytic proteases, particularly collagenases, than the conventional animal derived culture media.

The present invention also refers to a process for producing a supernatant of *Clostridium histolyticum* liquid culture comprising one or more collagenolytic and gelatinolytic proteases comprising the following steps: a) providing a sterile animal product-free culture medium; b) culturing *Clostridium histolyticum* stock culture in the culture medium of step (a), under anaerobic conditions at about 37° C. before reaching the stationary growth phase in order to obtain an inoculum; c) providing a sterile animal product-free culture medium according to present invention; d) adding to the culture medium of step (c) a volume of inoculum from step (b) equal to or lower than 10% of the final volume of the medium defined in (c); e) culturing the *C. histolyticum* obtained in (d) under anaerobic conditions at about 37° C. until the stationary growth phase; f) removing the cellular debris and other particulate matter from the liquid phase of the culture from step (e), yielding a supernatant comprising one or more collagenolytic and gelatinolytic proteases. Such process may comprise one or more additional steps for the purification of one or more collagenolytic and gelatinolytic proteases from the supernatant obtained in step (f).

The present invention also refers to a supernatant of a *Clostridium histolyticum* liquid culture comprising one or more collagenolytic and gelatinolytic proteases obtained according to the process mentioned above, and pharmaceutical compositions comprising, as active ingredient, a supernatant of *Clostridium histolyticum* liquid culture and pharmaceutically acceptable excipients.

The vitamins and the salts were tested in the following concentrations:

| Components | Quantities (mg/ml) |
|---|---|
| Salts * | |
| Potassium phosphate dibasic ($K_2HPO_4$) | 1.0 |
| Potassium phosphate monobasic ($KH_2PO_4$) | 1.0 |
| Magnesium sulphate ($MgSO_4 \cdot 7H_2O$) | 0.4 |
| Sodium chloride (NaCl) | 0.02 |
| Iron sulphate ($FeSO_4 \cdot 7H_2O$) | 0.02 |
| Manganese sulphate ($MnSO_4 \cdot 4H_2O$) | 0.02 |
| Vitamins ** | |
| Biotin | 0.00625 |
| Pimelic acid | 0.02 |
| Nicotinamide | 0.02 |
| Calcium pantothenate | 0.02 |
| Folic acid | 0.02 |
| Thiamine nitrate | 0.02 |
| Riboflavin | 0.02 |
| P-Aminobenzoic acid (PABA) | 0.02 |
| Amino acids - Aa*** | |
| Mix 20 Aa | 1/each |

Figure 6:
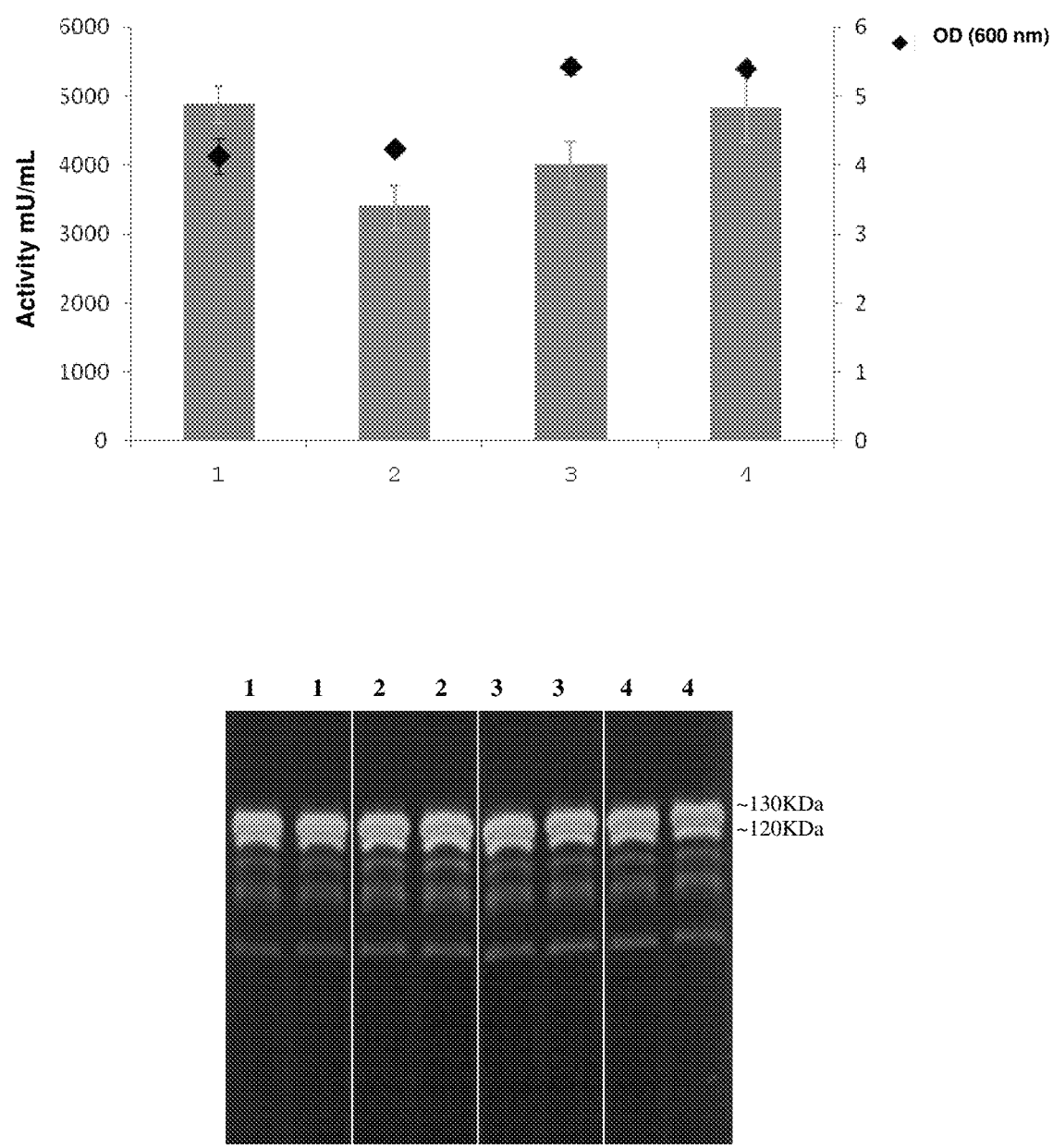

FIG. 6. Bacterial growth (OD) and enzymatic activity of *C. histolyticum* (ATCC 21000) cultures supplemented with inorganic salts, vitamins and amino acids. Culture media used are animal product-free and comprise: 30 g/L of soybean peptone (NZ SOY BL4), 30 g/L of yeast extract (YE 251), 0.625 g/L of cysteine hydrochloride and 3.75 g/L arginine hydrochloride. Enzymatic activity was analyzed through zymography gel (samples of the supernatant obtained for each culture medium were analyzed in duplicates). The bars (1-4) in the chart refer to:
1—Control Medium (Ctrl):
  vegetable peptone NZ-soy BL4 (30 g/L);
  Yeast extract YE 251 (30 g/L);
  Cysteine hydrochloride (0.625 g/L);
  L-arginine (3.75 g/L).
2—Ctrl+Vitamins
3—Ctrl+Phosphates
4—Ctrl+Vitamins+Phosphates FIG. 7. Collagenolytic and gelatinolytic activity of the supernatant of *C. histolyticum* (ATCC 21000) animal product-free liquid cultures containing vegetable peptone and yeast extract from different suppliers (3% w/v of vegetable peptone, 3% w/v of yeast extract, 0.0625% w/v of cysteine hydrochloride). Standard culture medium (comprising casein peptone) was used for comparison.

Figure 8:
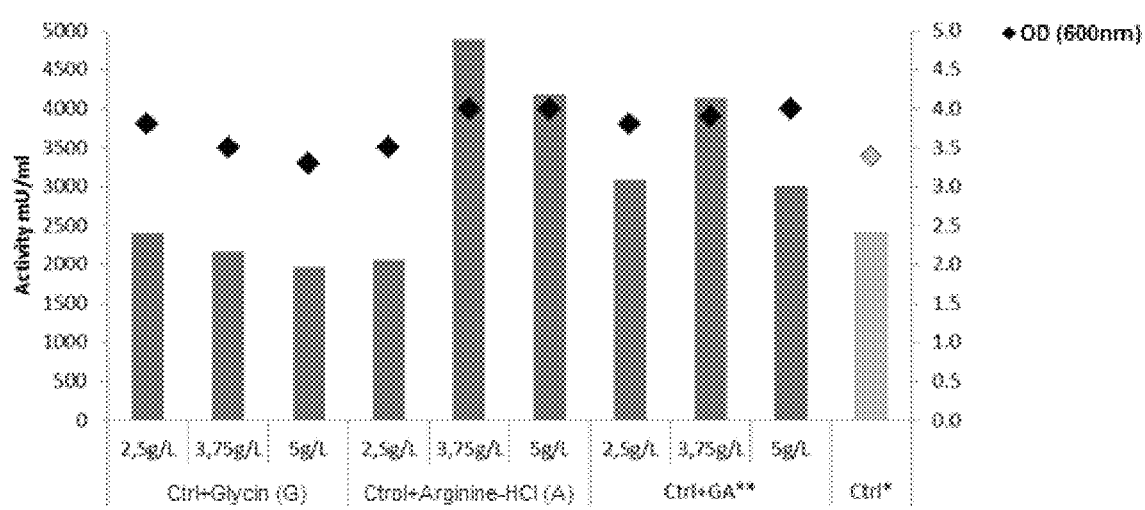

FIG. 8. Bacterial growth and collagenolytic and gelatinolytic activity of the supernatant of C. histolyticum (ATCC 21000) liquid culture using an animal product-free culture medium (30 g/L of soy peptone NZ SOY BL4, 30 g/L of YE251 and 0.625 g/L of cysteine) comprising, additionally, arginine, glycine or both. Horizontal axis label are as follow:

Ctrl*=NZ-SoyBL4 (30 g/L); Yeast extract YE 412 (30 g/L); Cysteine hydrochloride (0.625 g/L); and
GA**=Glycine+L-arginine-HCl FIG. 9. Bacterial growth and collagenolytic and gelatinolytic activity of the supernatant of C. histolyticum liquid culture using an animal product-free culture medium (3% w/v of soy peptone NZ SOY BL4, 3% w/v of YE251 and 0.0625% w/v of cysteine) comprising, additionally, amino acid pools (Groups 1 to 6). Enzymatic activity was analyzed through zymography gel. The Groups 1-6 and Control in the chart refer to:

| Group 1: | Glutamate/Proline/Glutamine/Arginine* |
| Group 2: | Aspartate/Asparagine/Lysine/Methionine/Threonine/Isoleueine* |
| Group 3: | Alanine/Valine/Leucine* |
| Group 4: | Serine/Glycine/Cysteine* |
| Group 5: | Phenylalanine/Tyrosine/Tryptophan* |
| Group 6: | Histidine* |
| Control: | NZ-Soy BL4 (3%); Yeast extract YE 251 (3%); cysteine hydrochloride (0.0625%). |

*Amino acids at 1 mg/ml each.

Figure 10:
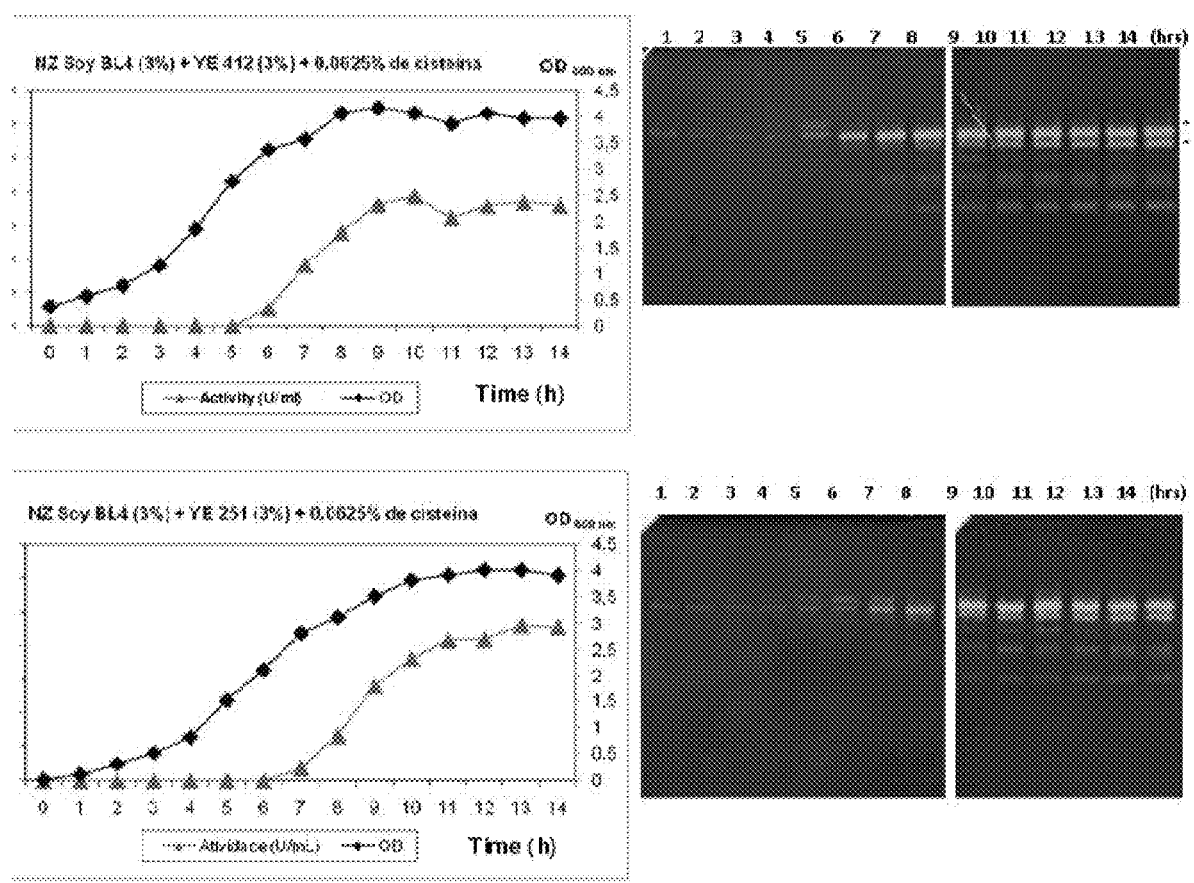

FIG. 10. Bacterial growth and collagenolytic and gelatinolytic activity of the supernatant of C. histolyticum bioreactor (3 L) liquid culture using an animal product-free culture medium (3% w/v of soy peptone NZ SOY BL4, 3% w/v of YE251 or YE 412 and 0.0625% w/v of cysteine). Enzymatic activity was analyzed through zymography gel.

Figure 11:
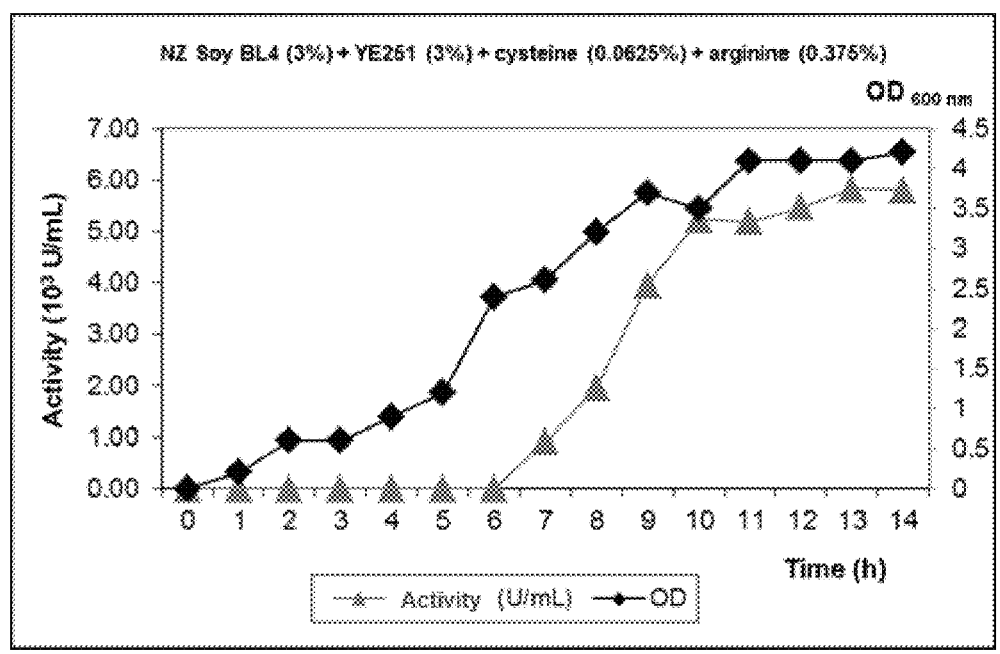
Figure 11:
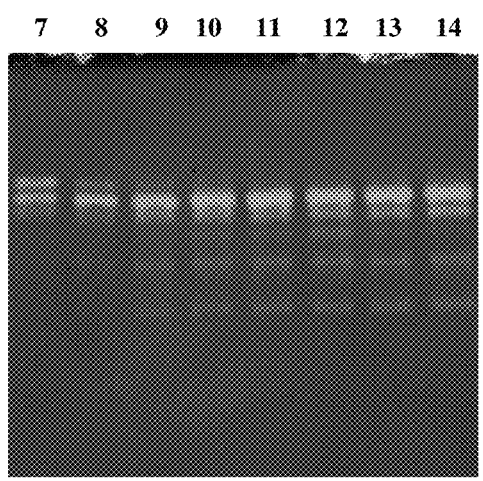
Figure 11:
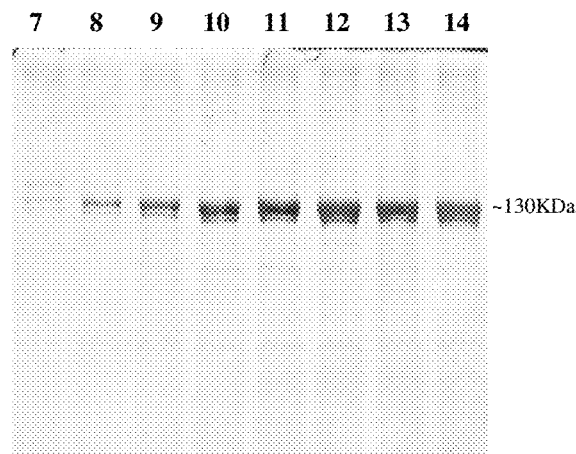

FIG. 11. Bacterial growth and collagenolytic and gelatinolytic activity of the supernatant of C. histolyticum bioreactor (3 L) liquid culture using an animal product-free culture medium (3% w/v of soy peptone NZ SOY BL4, 3% w/v of YE251 and 0.0625% w/v of cysteine and 0.375% w/v of arginine). Enzymatic activity was analyzed through zymography gel (B) and the protein profile was analyzed through SDS-PAGE gel (C) (analysis performed only after 7 hours of culture).

Figure 12:
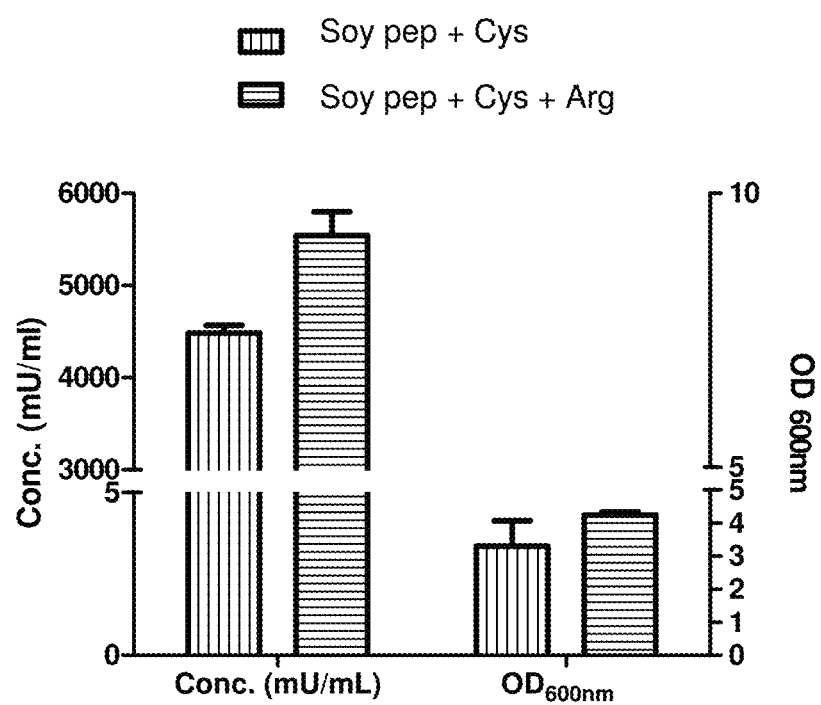

FIG. 12. Growth and collagenolytic and gelatinolytic activity of the supernatant of C. histolyticum (ATCC 21000) liquid culture (bioreactor—3 L) using an animal product-free culture media comprising: 3% w/v of soy peptone NZ SOY BL4, 3% w/v of YE251 and 0.0625% w/v of cysteine; or 3% w/v of soy peptone NZ SOY BL4, 3% w/v of YE251, 0.0625% w/v of cysteine and 0.375% w/v of arginine. Analysis performed with supernatant samples collected at the end of the culturing process.

Figure 13:
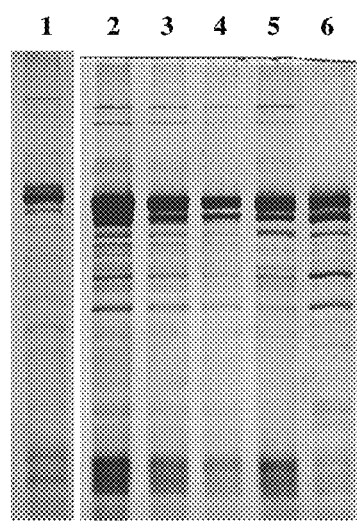

FIG. 13. Recovery of collagenolytic and gelatinolytic proteases from supernatant of C. histolyticum (ATCC 21000) liquid culture in animal product-free culture medium comprising 3% w/v of soy peptone NZ SOY BL4, 3% w/v of YE251, 0.0625% w/v of cysteine and 0.375% w/v of arginine. Protein profile was obtained through SDS PAGE of samples collected during the culture process. In the chart, the columns from 1 to 6 refer to:

| | Activity (U/mL) | Yield (%) |
|---|---|---|
| 1 - Supernatant (4x) | 908.578 | 100 |
| 2 - post-dialysis (4x) | 749.568 | 82.5 |
| 3 - post-dialysis (10x) | | |
| 4 - post-dialysis (25x) | | |
| 5 - post-dialysis (50x) | | |
| 6 - post-lyophilization (25x) | 798.649 | 87.35 |

Figure 14:
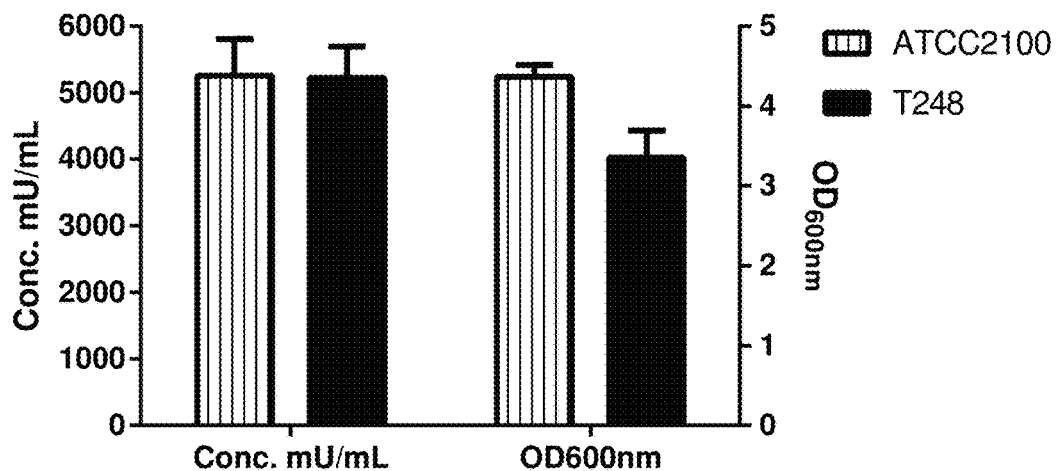
Figure 14:
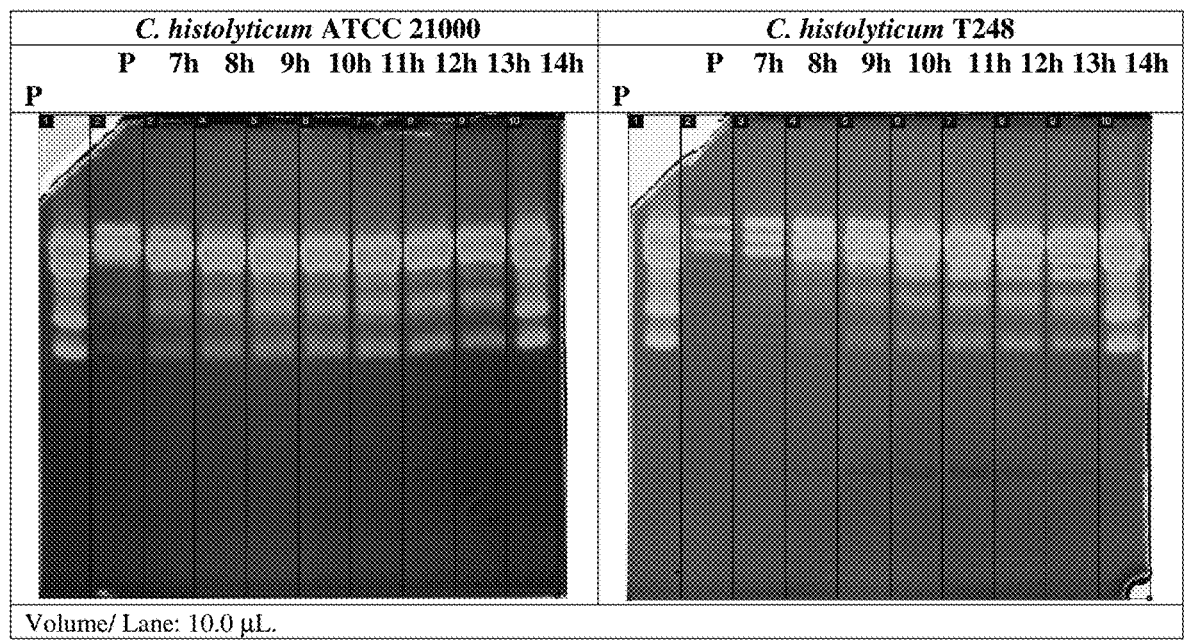

FIG. 14. Bacterial growth (DO 600 nm) and collagenolytic and gelatinolytic activity (mU/mL) of the supernatant of C. histolyticum ATCC 21000 and T248 liquid culture in animal product-free culture media comprising: 3% w/v of soy peptone NZ SOY BL4, 3% w/v of YE251, 0.0625% w/v of cysteine and 0.375% w/v of arginine. Cultures were carried out in bioreactor (3 L). Analyses were performed (14 h) at the end of the culture process.

DETAILED DESCRIPTION OF THE INVENTION

In order to guarantee a better understanding of the invention's scope, without making it a limiting factor, the specific terms related to the present invention are defined as follows.

"Proteases" (proteinases, peptidases or proteolytic enzymes, EC 3.4), according to present invention, are enzymes that cleave protein peptide bonds.

Clostridium histolyticum "Collagenases" type I and type II are defined accordingly to the description supplied by Bond M. D., van Wart, H. E., 1987, Biochemistry 23:3077-3085 and Bond, M. D., van Wart, H. E., 1984, Biochemistry, 23: 3085.

"Collagen proteins" or "collagen" refer to the main structural protein present in the skin and bones of most animals, which are important extracellular matrix components. Collagen molecules consist of 3 individual polypeptide chains (alpha chains) folded in a triple helix configuration stabilized by hydrogen bonds.

"Gelatin" refers to a partially hydrolyzed form of collagen.

"Collagenolytic and gelatinolytic activity" refers to the measure of collagen and/or gelatin degradation by proteases within a specified period of time. It is usually expressed in units/mL, units/L, units/mg of enzyme or units/g of enzyme. Collagenolytic and gelatinolytic activity can be determined through a variety of methodologies such as viscometric analysis, colorimetric (ninhydrin; Moore & Stein, JBC, 176, 367, 1948) or fluorimetric reactions (collagen and gelatin substrates marked with fluorescein; EnzChek®) among others. In the case in which the activity is quantified following a colorimetric protocol with ninhydrin, the activity is measured by the enzymatic hydrolysis of a synthetic substrate (Carbobenzoxy-Gly-Pro-Gly-Gly-Pro-Ala).

"Bacterial growth" is defined as the division of a bacterial cell in two identical daughter cells during a process called binary fission. The duplication of bacterial population occurs at each cell division, undergoing exponential growth. Exponential bacterial growth in a culture can be monitored through well-known methods, such as, direct count of bacterial cells (i.e. microscopy, flow cytometry), biomass quantification (milligrams, grams, kilos or tons), colony count, optical density (measured in spectrophotometer, wavelength of about 600 nm), nutrient consumption, among others. Bacterial growth can be characterized by four different phases: "lag phase", "exponential or log phase", "stationary phase" and "decline or death phase".

It is of common knowledge that during the "lag phase", the bacteria are adapting to growth conditions and are not yet able to perform cellular division. It is a period when cells are entering a maturity state. The "exponential or log phase" is a period characterized by duplication of bacterial population. If growth is not restricted, cell duplication continues in a constant rate, so both, the number of cells and growth rate, duplicate in each generation. The exponential growth phase is not sustained indefinitely since the growth medium has nutritional restraints and the metabolites produced by bacterial cells during cellular division are often toxic. Thus, the growth rate tends to decrease and the bacterial growth enters in the "stationary phase". This phase is characterized by resource depletion in the culture medium. In the "decline or death phase", bacteria deplete completely the remaining nutrients in the culture medium and die.

"Pre-inoculum" is defined as a suspension of microorganisms obtained from a stock culture that will be used to "inoculum" production.

"Inoculum" is a suspension of microorganisms with a specific concentration to be used for growth and/or fermentation on a larger scale (greater volume of culture medium) than the initial one.

"Anaerobic condition" and "anaerobiosis" is defined as the maintenance of a substantially oxygen-free culture condition.

"Fresh culture medium" refers to any culture medium for microorganism growth or fermentation that has not been previously used, as a culture medium containing integrally all of its components.

"Freezing medium" characterizes a composition capable of maintaining a microorganism's viability after freezing or lyophilization and, thus, preserve its growth and fermentation capacity after long-term storage. The storage of the microorganism on the freezing medium can be performed on temperatures that are suitable for its cryopreservation. Moreover, it is also possible to lyophilize the microorganism in the freezing medium before storage. In the present invention, the freezing medium is free from animal derived components and contains, in addition, a cryopreservation agent.

"Cryopreservation agent", or cryoprotectant, is a substance intended to protect the microorganism during a freeze-thaw process allowing it to maintain cell viability after freezing. Some common cryopreservation agents used for microorganism storage are: sucrose, glycerol, dimethyl sulfoxide (DMSO), among others.

"Stock or storage culture" refers to a fraction of microorganism in freezing medium stored for a determined period of time.

"Supernatant" is used hereafter to describe the liquid phase of a microorganism culture medium (growth or fermentation medium), free from cell debris, particulate or solid material. The supernatant can be obtained by well-known centrifugation and/or filtration procedures.

"Peptones" are characterized in the present invention as mixtures of compounds obtained by protein hydrolysis (proteins fragments, whose composition depends on the protein source used for hydrolysis). Commonly, peptones are obtained by acid or enzymatic hydrolysis of natural products, such as animal or vegetable tissues, as well as milk or microbial cultures.

The protein source of animal derived peptones is often a by-product of meat and dairy production. Therefore, its hydrolysis results in several other compounds, apart from peptides and amino acids, such as fats, metal ions, salts and vitamins.

"Animal Product-Free" refers to the absence of any animal derived product, component or compound. "Animal" includes mammals, birds, reptiles, fishes, amphibians, arthropods, withal other animal species. "Animal" excludes microorganisms such as bacteria and yeasts. Thus, "Animal Product-Free" can comprise proteases derived from bacteria of the genus *Clostridium*, such as *C. histolyticum*. A composition "animal Product-free" does not include animal derived proteins, such as: immunoglobulin, meat digests and by-products, and dairy products and their derivatives.

In the context of this invention "component", "ingredient", "product" or "source" "of non-animal derived" are the preferred sources of ingredients for the *Clostridium histolyticum* culture medium, including vegetables, microorganisms (e.g., yeast) and synthetic compounds.

"Standard or conventional culture medium" refers to the culture medium for growth and/or fermentation of bacteria of the genus *Clostridium*, in particular *C. histolyticum*, comprising animal derived components, including peptone proteose, tryptic digests of casein or meat, casein peptone, among others.

Invention Description

It is well known that animal derived peptones are essential ingredients of the culture medium to *Clostridium histolyticum* growth, having a strong influence on the production of gelatinolytic and collagenolytic proteases. However, regarding the protease for therapeutic use in humans, it is desired to avoid animal derived ingredients throughout the entire production process, eliminating the risk of pathogens inter-specific horizontal transmission and pathological immune responses against animal derived antigenic peptides that may be present in the final product, even after several purification steps.

Thereby, this invention describes a *Clostridium* animal product-free culture medium for growth and collagenolytic and gelatinolytic protease production. Most preferably, the present invention describes a culture medium for *C. histolyticum*.

Bacterial growth and collagenolytic and gelatinolytic protease production using the animal product-free culture medium as described in this invention were compared to the results of cultures with animal derived medium comprising i.e proteose peptone or casein hydrolysate (standard or conventional culture medium).

Particularly, the culture medium described in the present invention yields a supernatant with higher collagenolytic and gelatinolytic activity than the one obtained from *Clostridium histolyticum* culture using standard culture medium (comprising animal derived peptones).

Thereby, this invention presents an animal product-free culture medium for *Clostridium*, most particularly *C. histolyticum*, comprising water, non-animal derived peptone, or its derivatives, yeast extract and the amino acids cysteine and arginine, or pharmaceutically acceptable salts thereof.

The culture medium of the present invention can additionally comprise one or more additive selected from the group consisting of agent for pH adjustment within the range of 7 to 8, reducing agent, inorganic salts, vitamins and mixtures thereof.

Optimum bacterial growth rates and collagenolytic and gelatinolytic proteases production, mainly collagenases, are achieved using the culture medium of this invention with a pH ranging from 7.0 to 8.0, preferably around 7.0. pH adjustment must be performed after sterilization and before initiating *C. histolyticum* culture, through aqueous solutions of a pH adjustment agent known by those skilled the art, e.g., ammonium sulphate, NaOH, sulphuric or nitric acid, among others.

The additives (reducing agents, inorganic salts and vitamins) that can be included on the animal product-free culture medium are selected among substances known by those skilled in the art.

The reducing agent, according to this invention, is selected from the group consisting of sodium thioglycolate, sodium bisulphite, iron salts, glucose and mixtures thereof.

Additionally, according to this invention, the inorganic salts are selected from the group consisting of NaCl, KCl, $Na_2HPO_4$, $NaH_2PO_4$, $KH_2PO_4$, $K_2HPO_4$, $MgSO_4$, $FeSO_4$, $MnSO_4$ and mixtures thereof.

Vitamins, according to the present invention, is selected from the group consisting of biotin, pimelic acid, nicotinamide, calcium pantothenate, folic acid, thiamine nitrate, riboflavin, p-aminobenzoic acid (PABA) and mixtures thereof.

Non-animal derived peptones evaluated as ingredients for *Clostridium histolyticum* culture medium are listed in Table 1.

TABLE 1

Non-animal derived peptones evaluated as ingredients for *Clostridium histolyticum* culture medium as described in the present invention.

| Non-animal derived peptones | Supplier |
| --- | --- |
| Amysoy ® | Sheffield ™ Bioscience (Kerry, USA) |
| HYP A ® | BioSpringer (France) |
| Hy-Pep 1510 ® | Sheffield ™ Bioscience (Kerry, USA) |
| Hy-Pep 1511 ® | Sheffield ™ Bioscience (Kerry, USA) |
| Hy-Pep 4601 ® | Sheffield ™ Bioscience (Kerry, USA) |
| Hy-Pep 4605 ® | Sheffield ™ Bioscience (Kerry, USA) |
| Hy-Pep 5603 ® | Sheffield ™ Bioscience (Kerry, USA) |
| Hy-Pep 7504 ® | Sheffield ™ Bioscience (Kerry, USA) |
| Hy-soy ® | Sheffield ™ Bioscience (Kerry, USA) |
| NZ-Soy BL4 ® | Sheffield ™ Bioscience (Kerry, USA) |
| NZ-Soy BL7 ® | Sheffield ™ Bioscience (Kerry, USA) |
| Soy peptone 312 - AF ® | Biotecnica Internacional (Mexico) |

Non-animal derived peptones can also be obtained from other suppliers, such as: Soy Peptone® (Gibco), Bac-soytone® (Difco), SE50M® (DMV), Soy peptone 312® (Biotecnica International, Mexico), SE50MAF-UF® (DMV), Stedygro Soy® and Proyield Soy®.

The animal product-free culture medium for *Clostridium histolyticum* comprises a non-animal derived peptone that is a vegetable peptone selected from the group consisting of soy, cotton, wheat, sunflower, rice, peanuts, fava beans, peas, potato, corn and mixtures thereof. Preferably, the vegetable peptone is soy, cotton or wheat peptone, or its mixtures. Most preferably, the vegetable peptone is soy peptone.

This application discloses surprisingly that peptones or other animal derived components are not essential for *Clostridium histolyticum* culture, and that the animal product-free culture medium of the present invention yields collagenolytic and gelatinolytic proteases production superior to that obtained in conventional culture medium (containing animal derived components).

According to the present invention, vegetable peptones from different suppliers can be used in the *Clostridium histolyticum* animal product-free culture medium. Preferably, the vegetable peptones are hydrolyzed and its production process is also animal product-free.

The vegetable peptone, according to this invention, is selected from the group consisting of Hy Soy®, Soytone®, Amisoy®, NZ Soy BL4®, NZ Soy BL7®, Hy Pep 1510®, Hy Pep 1511®, Hy Pep 5603®, Hy Pep 7504®, Stedygro Soy®, SE50M®, Proyield Soy®, SE50MAF-UF®, Soy peptone 312, Hy Pep 4601 and mixtures thereof.

Preferably, the vegetable peptone is selected from the group consisting of Hy Pep 4601®, NZ soy BL4®, HyPep 1511® and Hy Pep 7504®. Most preferably, the vegetable peptone is NZ soy BL4®.

Besides non-animal or vegetable derived peptones, the *Clostridium histolyticum* culture medium described in the present invention contains yeast extract as a critical ingredient. Commercial suppliers evaluated for this ingredient are listed in Table 2.

TABLE 2

Yeast extracts evaluated as ingredients for *Clostridium histolyticum* culture medium described on this invention.

| Yeast Extract | Supplier |
| --- | --- |
| Bacto YE ® | BD Bioscience (USA) |
| Hy-Pep YE ® | Sheffield ™ Bioscience (Kerry, USA) |
| Hy-Yeast 412 ® | Sheffield ™ Bioscience (Kerry, USA) |
| Hy-Yeast 413 ® | Sheffield ™ Bioscience (Kerry, USA) |
| Hy-Yeast 502 ® | Sheffield ™ Bioscience (Kerry, USA) |
| Hy-Yeast 501 ® | Sheffield ™ Bioscience (Kerry, USA) |
| Hy-Yeast 503 ® | Sheffield ™ Bioscience (Kerry, USA) |
| Prodex 710 SD ® | BioSpringer (France) |
| Prodex NS70SD ® | BioSpringer (France) |
| Pronal 5001 ® | BioSpringer (France) |
| YE 11 ® | Sheffield ™ Bioscience (Kerry, USA) |
| YE151 ® | Biotecnica Internacional (Mexico) |
| YE251 ® | BioSpringer (France) |
| YE 70161 ® | Fluka (Sigma-Aldrich GmbH) |
| YE Y4250 ® | Sigma-Aldrich GmbH |
| Synth ® | Synth ® (Brazil) |
| YE 207 ® | BioSpringer (France) |
| YE 5114 ® | Vetec Quimica Fina (Brazil) |

Preferably, according to the present invention, the yeast extract is selected from the group consisting of Bacto YE®, Hy-Pep YE®, Hy-Yeast 412®, Hy-Yeast 413®, Hy-Yeast 502®, Hy-Yeast 501®, Hy-Yeast 503® Prodex 710 SD®, Prodex NS70SD®, Pronal 5001®, YE 11®, YE 151®, YE 251®, YE 70161®, YE Y4250®, Synth®, YE 207®, YE 5114® and mixtures thereof. Most preferably, the yeast extract is YE 251®.

Regarding the amino acids, arginine is L-arginine and cysteine is L-cysteine or its pharmaceutically acceptable salts. Preferably, the pharmaceutically acceptable salts are cysteine hydrochloride and arginine hydrochloride.

The culture medium of the present invention comprises non-animal derived peptone at a concentration range from 0.5% to 5% w/v, yeast extract at a concentration range from 0.5% to 5% w/v, cysteine, or its pharmaceutically acceptable salts, at a concentration range from 0.01% to 0.1% w/v, and arginine, or its pharmaceutically acceptable salts, at a concentration range from 0.1% to 1% w/v.

Preferably, the culture medium comprises non-animal derived peptone at a concentration range from 1% and 4% w/v, yeast extract at a concentration range from 1% and 4% w/v, cysteine, or its pharmaceutically acceptable salts, at a concentration range from 0.03% to 0.07% w/v, and arginine, or its pharmaceutically acceptable salts, at a concentration range from 0.25% to 0.7% w/v. Most preferably, the non-animal derived peptone is at a concentration of 3% w/v, yeast extract is at a concentration of 3% w/v, cysteine, or its pharmaceutically acceptable salts, is at a concentration of 0.0625% w/v, and arginine, or its pharmaceutically acceptable salts, is at a concentration of 0.375% w/v.

The culture medium, according to the present invention, must be sterilized before the *C. histolyticum* inoculum. Media sterilization can be performed through methods known by those skilled in the art, for example, moist heat autoclaving or filtration. Thus, the culture medium described in this invention is characterized by being sterile. Preferably, the animal product-free culture medium of the present invention is characterized by being liquid.

The culture medium, according to the present invention, is used in a process for producing a supernatant of *Clostridium histolyticum* liquid culture comprising one or more collagenolytic and gelatinolytic proteases.

*C. histolyticum*, when cultured in the animal product-free liquid medium presented herein, secrete such proteases into the liquid phase. Collagenases are the main protein components in the supernatant produced by such *C. histolyticum* culture.

In another embodiment, a process for producing a supernatant of *Clostridium histolyticum* liquid culture comprising one or more collagenolytic and gelatinolytic proteases is provided, which comprises the use of an animal product-free culture medium according to the present invention. The process for producing a supernatant of *Clostridium histolyticum* liquid culture comprising one or more collagenolytic and gelatinolytic proteases comprising the following steps:
  a) providing a sterile animal product-free culture medium;
  b) culturing *Clostridium histolyticum* stock culture in the culture medium of step (a), under anaerobic conditions at about 37° C. before reaching the stationary growth phase in order to obtain an inoculum;
  c) providing a sterile animal product-free culture medium according to present invention;
  d) adding to the culture medium of step (c) a volume of inoculum from step (b) equal to or lower than 10% of the final volume of the medium defined in (c);
  e) culturing the *C. histolyticum* obtained in (d) under anaerobic conditions at about 37° C. until the stationary growth phase;
  f) removing cellular debris and other particulate matter from the liquid phase of the culture from step (e), yielding a supernatant comprising one or more collagenolytic and gelatinolytic proteases.

Anaerobic conditions, as required in steps (b) and (e) can be attained through methods well known by those skilled in the art, including but not limited to the ones described hereafter. For instance, the anaerobic conditions in steps (b) and (c), can be maintained through the addition of nitrogen gas to the culture medium.

The purpose of culture medium referred in step (a) is to increase cell count from a stock culture, which is stored under appropriate conditions for maintaining cell viability. Preferably, the stock culture is maintained at −80° C. in an animal product-free culture medium containing one or more cryopreservation agents. In order to achieve *C. histolyticum* best growth rates in an animal product-free medium, the stock medium is also free of animal derived components.

The stock culture is produced from an animal product-free culture medium comprising vegetable peptones, preferably soy peptone or its derivatives, yeast extract, cysteine, as well as a cryopreservation agent, within a pH range from 6.5 to 8.0. Cryopreservation agents (cryoprotectant) for microorganisms, mainly bacteria, are broadly known by person skilled in the art and can be selected from the group consisting of glycerol, sucrose, dimethyl sulfoxide and glucose. The amount of cryoprotectant added to the stock culture varies depending on the bacterial strain and must be correctly adjusted prior to preparing the microorganism cell bank (master cell bank and working cell bank).

The purpose of the growth phase (step (b)) is to increase the amount of viable microorganisms for collagenolytic and gelatinolytic proteases production, which occurs in step (e). Additionally, the growth phase allows the dormant microorganisms in the stock culture to grow actively and secrete collagenolytic and gelatinolytic proteases at step (e). The sterile and animal product-free culture medium employed in step (a) comprises water, vegetable based peptone, yeast extract and cysteine. Specifically, the sterile and animal product-free culture medium employed in step (a) comprises water, 0.5% to 5% w/v of vegetable peptone, 0.5% to 5% w/v of yeast extract, 0.01% to 0.1% w/v of cysteine or its pharmaceutically acceptable salts and pH ranging from 6.5 to 8.0. Preferably, the culture medium of step (a) comprises water, 3% w/v of vegetable peptone, 3% w/v of yeast extract, 0.0625% w/v of cysteine or its pharmaceutically acceptable salts and pH ranging from 6.5 to 8.0.

As it will be noticed in the Examples 1 and 2, there is no need of supplementing the animal product-free culture medium with arginine in order to achieve higher growth rate than the one observed in standard culture medium (with animal derived peptone). Therefore, the preferred culture medium described for step (a) has been defined considering only the minimal components for bacterial growth. However, similar results are observed when the medium contains, not only the described essential components, but also arginine and other additives (inorganic salts, vitamins and reducing agents).

The arginine amino acid is essential for the surprising results of the present invention regarding the production of collagenolytic and gelatinolytic proteases (step (e)). The production of *C. histolyticum* proteases is much higher with animal product-free culture medium comprising arginine and cysteine than the one obtained with animal product-free culture medium supplemented only with cysteine or with the conventional culture medium containing animal derived components.

Thus, the sterile animal product-free culture medium employed in step (c) of the process for producing a supernatant of *Clostridium histolyticum* liquid culture comprising one or more collagenolytic and gelatinolytic proteases comprises water, vegetable peptone, yeast extract, cysteine, arginine and pH ranging from 7.0 to 8.0.

Preferably, the sterile animal product-free culture medium described in step (c) comprises water, 3% w/v of vegetable peptone, 3% w/v of yeast extract, 0.0625% w/v of cysteine or its pharmaceutically acceptable salts, 0.375% w/v of arginine or its pharmaceutically acceptable salts and pH ranging from 7.0 to 8.0.

Bacterial growth can be monitored by measuring the optical density of the culture medium during the process described above (steps (b) and (e)) using a spectrophotometer (wavelength 600 nm) according to methods well known by those skilled in the art.

The *C. histolyticum* culture during step (b) may occur in one or more steps. Preferably, the step (b) of the process for producing a supernatant of *Clostridium histolyticum* liquid culture comprises at least the following steps: 1) culturing a stock culture in the culture medium from step (a) in a ratio of 0.1:1 v/v for about 16 hours in order to obtain a pre-inoculum; 2) adding to the pre-inoculum obtained in step 1 an amount of culture medium from step (a) equal to or higher than the double of the culture medium volume from step (1) and maintaining the culture for about 12 hours in order to obtain an inoculum.

It is essential that the growth during step (b) does not lead to cell lysis before its inoculation into the culture medium in step (c), guaranteeing the cell viability of the inoculum.

The process for producing a supernatant of *Clostridium histolyticum* liquid culture can comprised only steps from (c) to (f), culturing the *C. histolyticum* stock culture directly in the culture medium described in step (c), without producing an inoculum.

Preferably, the process for producing a supernatant of *Clostridium histolyticum* liquid culture comprises, during step (e), the addition of one or more agents to pH adjustment in sufficient amount to maintain the culture medium pH from 6.5 to 8.0.

In the present invention, during step (f) of the process for obtaining *C. histolyticum* collagenolytic enzymes, the separation of cellular debris or other particulate matter from the liquid phase of the culture can be performed through different techniques of filtration, centrifugation or chromatographic purification known on the state of the art and not limited to tangential filtration, centrifugation, chromatography gel filtration, among others.

Thus, the step (f) of the process for producing a supernatant of *Clostridium histolyticum* liquid culture is carried out through filtration, centrifugation, or both.

In addition, the process for producing a supernatant of *Clostridium histolyticum* liquid culture comprises one or more additional steps for the purification of one or more collagenolytic and gelatinolytic proteases from the supernatant obtained in step (f). Purification can be performed through various methods of filtration, chromatographic purification or saline precipitation, not limited to ammonium sulfate precipitation, tangential filtration, ion-exchange chromatography, affinity chromatography, gel filtration chromatography, among others, individually or combined.

According to the present invention, the supernatant of *C. histolyticum* liquid culture is a complex mixture including, not only collagenolytic and gelatinolytic proteases, mainly collagenases, but also other proteins, bacterial metabolites, culture medium components, among other substances.

Thus, an additional aspect of the present invention refers to a supernatant of *Clostridium histolyticum* liquid culture comprising one or more collagenolytic and gelatinolytic proteases, which is produced by the process described above.

The supernatant, according to this invention, can be directly purified in order to obtain one or more collagenolytic and gelatinolytic proteases.

Particularly, the supernatant, according to the present invention, comprises, after purification, from 20 to 90% of collagenases.

Alternatively, the supernatant can be stored on a frozen or lyophilized form, without lost its collagenolytic and gelatinolytic activity.

In another embodiment, the use of a supernatant of *Clostridium histolyticum* liquid culture obtained through the process described in the present invention is for the manufacture of a medicament for treatment of diseases benefiting from collagenolytic and gelatinolytic activity of proteases. Particularly, the invention describes the use of a supernatant of *C. histolyticum* liquid culture for the manufacture of a medicament for treatment of collagen-mediated diseases or pathological conditions of a human body associated with erratic accumulation of fibrous tissue rich in collagen. In addition, the invention describes the use of a supernatant of *C. histolyticum* liquid culture for the manufacture of a medicament for treatment of necrotic tissue and/or healing processes. Burns and skin lesions of diverse nature are examples of situations where necrotic tissue treatment is necessary.

Besides the use of a supernatant of *C. histolyticum* liquid culture is for the manufacture of a medicament for enzymatic debridement. This invention also discloses a pharmaceutical composition comprising as active ingredient a supernatant of *Clostridium histolyticum* liquid culture obtained from the process described herein and pharmaceutically acceptable excipients. The pharmaceutical composition can include one or more pharmaceutically acceptable excipients, buffers, carriers, stabilizers, preservatives and thickeners. The pharmaceutical composition, according to the invention, is for administration in animal or human for therapeutic or cosmetic use.

According to this invention, the pharmaceutical compositions comprising as active ingredient a supernatant of *Clostridium histolyticum* liquid culture can be administered through oral, sublingual, nasal, intravenous, intramuscular, intraperitoneal, intrarticular, subcutaneous, dermal, transdermal, among others. Preferably, the pharmaceutical composition, according to the present invention, is formulated for subcutaneous, dermal and transdermal administration.

Most preferably, the pharmaceutical composition, according to the present invention, is for topical use and comprises from 0.2 U to 1.8 U of collagenase per gram of composition (quantified through ninhydrin colorimetric method).

The carriers or pharmaceutically acceptable excipients are selected according to the final pharmaceutical form, which could be capsules, tablets, oral solutions, solutions for nasal administration, injectable solution for intramuscular, intravenous, cutaneous or subcutaneous administration or solutions, ointments or creams for topical use, among others. Thus, the pharmaceutical compositions of this invention comprise as active ingredient a supernatant of *Clostridium histolyticum* liquid culture and pharmaceutically acceptable excipients or carriers in the form of a cream or ointment formulation, lyophilized or aqueous solutions. Pharmaceutically acceptable excipients, carriers or stabilizers do not demonstrate toxicity to the patient at the dosages and concentrations employed and can include buffers such as phosphate, citrate, and other organic acids; antioxidants such as ascorbic acid and methionine; preservatives such as octadecyldimethylbenzyl ammonium chloride, hexamethonium chloride, benzalkonium chloride, benzethonium chloride, phenol, butyl alcohol, benzyl alcohol, alkyl parabens such as methyl- and propylparaben, catechol, resorcinol, cyclohexanol, 3-pentanol, and m-cresol; amino acids, monosaccharides, disaccharides, and other carbohydrates such as glucose, mannose, sucrose, mannitol, or sorbitol; polysaccharides (such as the polysaccharide hydrophilic Ficoll®); polymeric excipients such as polyvinylpyrrolidones, dextrins, polyethylene glycols; flavoring agents, sweeteners; anti-static agents; chelating agents such as EDTA or EGTA; salts releasing ions like sodium; metal complexes; non-ionic polysorbates such as "TWEEN 20" and "TWEEN 80"; lipids such as phospholipids, fatty acids and steroids such as cholesterol. Methods for the preparation of pharmaceutical compositions are well known to those skilled in the art.

Such pharmaceutical compositions can be used in the treatment of diseases benefiting from collagenolytic and gelatinolytic activity of *C. histolyticum* proteases, in the treatment of pathological conditions of the human body associated with excessive collagen deposition and erratic accumulation of fibrous tissue rich in collagen, treatment of necrotic tissue and healing process and treatment of enzymatic debridement.

C. histolyticum culture supernatant, as well as collagenolytic and gelatinolytic proteases, mainly collagenases, produced according to the process described in this invention does not exhibit toxicity, as observed by cytotoxicity and dermal toxicity studies.

The following examples are provided for a better understanding of the present invention, and are not intended to limit its scope.

Figure 1:
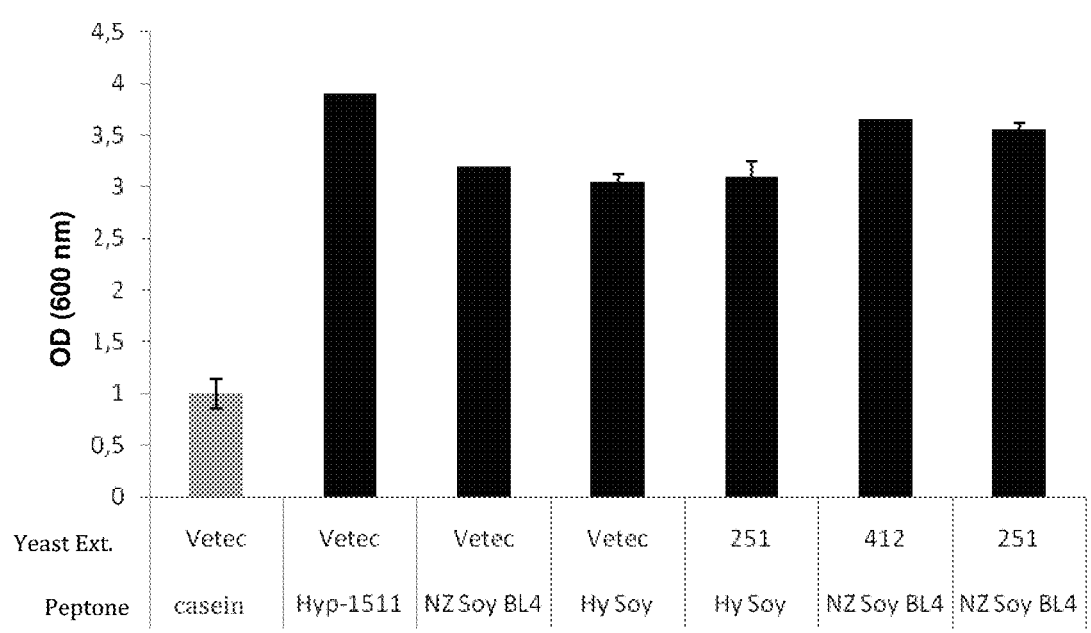
FIG. 1. Bacterial growth (optical density 600 nm) of *C. histolyticum* (ATCC 21000) in animal product-free culture media (3% w/v of vegetable peptone, 3% w/v of yeast extract, 0.0625% w/v of cysteine hydrochloride) containing vegetable peptone and yeast extract from different suppliers. Standard culture medium (comprising casein peptone) was used for comparison.
Figure 2:
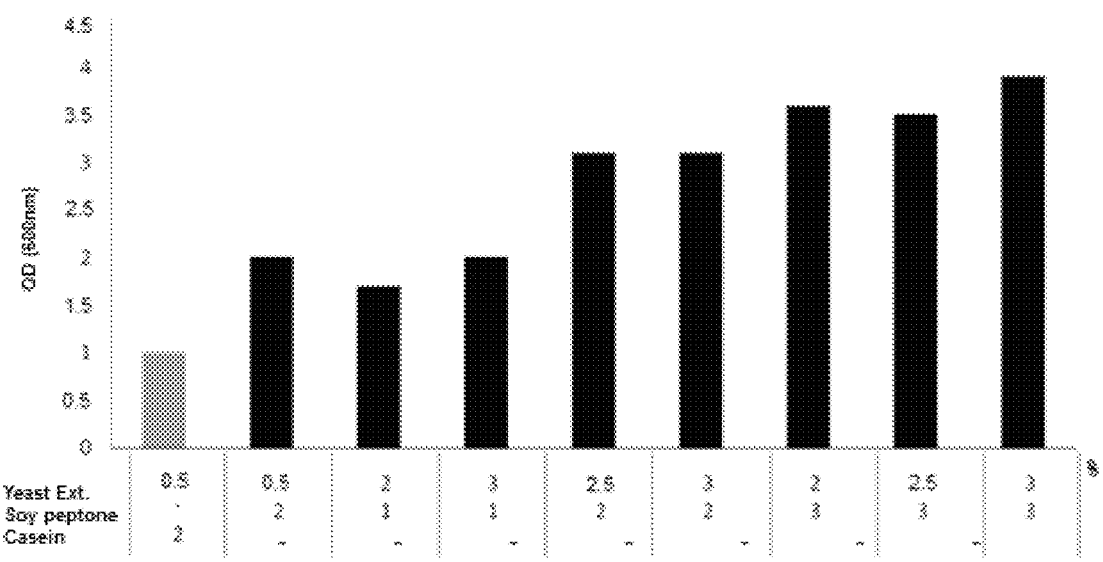
FIG. 2. Bacterial growth (optical density 600 nm) of *C. histolyticum* (ATCC 21000) in animal product-free culture media distinguished by the concentration of vegetable peptone (HY Pep 1511) and yeast extract (YE5114) used. The animal product-free culture media contain 0.0625% w/v of cysteine hydrochloride. Standard culture medium (comprising casein peptone) was used for comparison.
Figure 9:
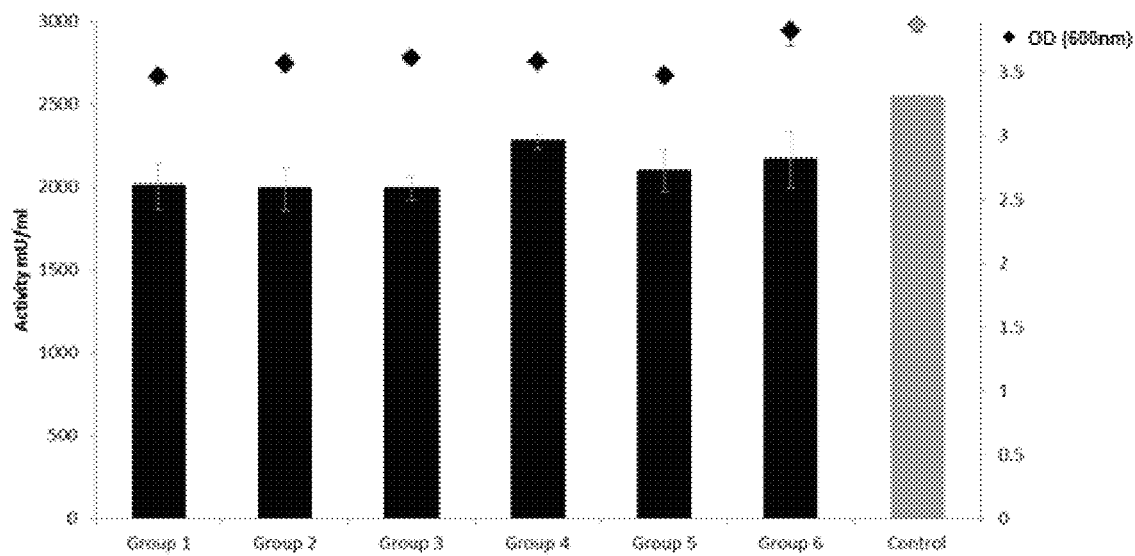
Figure 9:
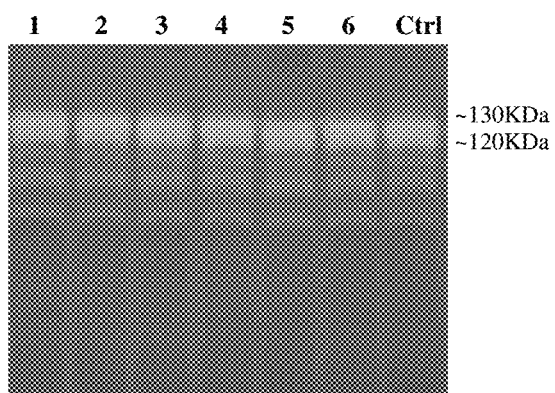

Examples 1-4 demonstrate the preparation of animal product-free culture media, according to the present invention, and C. histolyticum growth and production of collagenolytic and gelatinolytic proteases. Results obtained confirm the effectiveness of the animal product-free culture medium to provide C. histolyticum growth in comparison with standard culture medium, even without arginine in its composition (FIGS. 1 and 2). The importance of the yeast extract in the culture medium can be observed in FIG. 3, and the preferred pH range for C. histolyticum growth is exemplified in FIG. 4. FIGS. 5 and 6 clearly demonstrate that supplementing the animal product-free medium with vitamin and inorganic salts yields no improvement in cell growth or in protein expression. However, the addition of arginine in the animal product-free culture medium proposed herein is critical for increasing protease expression (yielding a supernatant with higher collagenolytic and gelatinolytic activities), as demonstrated in FIGS. 7 and 8. Evidence of the importance of arginine and cysteine for producing collagenolytic and gelatinolytic proteases in the animal product-free culture medium is shown in FIG. 9.

Moreover, the examples cited above clearly portray the quality of the supernatant obtained by culturing C. histolyticum in the animal product-free medium of the present invention. The quality of the supernatant is demonstrated by the prevailing concentration of high molecular weight proteases, which is associated with the C. histolyticum collagenases, whose enzymatic activity is also demonstrated.

Example 5 shows the results of bioreactor (3 L) cultures with the animal product-free culture medium described in the present invention. FIG. 10 shows the results of a culture using an animal product-free culture medium without arginine, demonstrating the importance of this amino acid to the protease production (FIG. 11). FIG. 12 shows a comparative graph between animal product-free culture media with and without arginine. The parameters considered in this analysis were bacterial growth rate and enzyme production.

Example 6 describes a recovery process to the collagenolytic and gelatinolytic proteases from the supernatant of C. histolyticum culture in animal product-free medium described in the present invention. The supernatant obtained does not have precipitates, facilitating its manipulation. The results of the collagenolytic enzymes recovery by precipitation with ammonium sulfate, followed by dialysis and lyophilization are shown (FIG. 13).

Example 7 presents a pharmaceutical composition for topical use comprising a supernatant of C. histolyticum animal product-free liquid culture. The stability of the compositions is also described, demonstrating the quality of the product obtained by the described fermentative process and defining one more advantage of the present invention.

Example 8 describes repeated dose dermal toxicity (21 days) in rats (male and female), demonstrating the absence of toxicity of the pharmaceutical compositions prepared with collagenolytic enzymes obtained through tangential filtration and lyophilization of the supernatant of C. histolyticum animal product-free liquid culture, according to the present invention. The absence of toxicity of the pharmaceutical compositions emphasizes the quality of the enzymatic profile of the supernatant of C. histolyticum animal product-free liquid cultures, according to the present invention.

Example 9 shows the results from cultures of two C. histolyticum strains, ATCC21000 and T248, in a 3 L bioreactor using animal product-free medium as described in the present invention. FIG. 14 shows the comparative results, demonstrating an equivalent production of colagenolytic and gelatinolytic proteases by both strains.

Example 10 shows the cytotoxicity test of the collagenolytic and gelatinolytic proteases obtained from the supernatant of liquid cultures of the two C. histolyticum strains (ATCC 21000 and T248) in animal product-free culture medium.

EXAMPLES

The examples below are merely illustrative, and must be applied solely for a better understanding the present invention.

C. histolyticum strains may be obtained from several sources, including the American Type of Culture Collections (ATCC). Several Clostridium histolyticum strains have already been applied with the intent of obtain collagenase; hence the present invention does not limit itself only to the strain utilized in the examples below.

The ATCC 21000 [non-mobile mutant of a mobile wild-type strain, isolated from soil (ATCC 21000™)] Clostridium histolyticum strain was used in almost all examples presented herein. The reason for such is due to the fact that this strain is known for yielding high amounts of good quality collagenolytic and gelatinolytic enzymes. The culture medium advised by ATCC for its propagation includes animal derived peptones, inorganic salts and leaver digest (culture medium Reinforced Clostridial Medium—RCM—Oxoid CM149, pH 8.0; anaerobic conditions).

In addition, Examples 9 and 10 show the results of cultures using animal product-free medium as described herein for the T248 Clostridium histolyticum strain, isolated from a superficial sample of soil (Espirito Santo do Pinhal/SP, Brazil). The T248 strain was characterized morphologically (gram positive spore—forming bacillus), biochemically (facultative anaerobic, which degrades gelatins) and genetically (tpi gene, ribosomal 16S and 23S), with the complete sequencing of ColG and ColH genes, exclusive to C. histolyticum strains encoding collagenase class I and II. The strain was also characterized phylogenetically using 16S-23S intergenic region sequences.

Example 1. Process for Producing Standard and Animal Product-Free Culture Media for Clostridium histolyticum The standard or conventional culture medium was prepared using the following ingredients (grams or milligrams per liter of medium): Proteose peptone n. 3 or casein peptone (20 g); yeast extract (5 g); glucose (5 g); sodium thioglycolate (250 mg), pH 7.0 (adjusted with 5M NaOH).

The animal product-free culture medium was prepared using the following ingredients (grams or milligrams per liter of medium): vegetable derived peptone (10-40 g); yeast extract (0-30 g); cysteine hydrochloride (625 mg), pH 7.0 (adjusted with 5M NaOH).

All components, except glucose which is present only in the standard medium, were dissolved in water and the pH was adjusted to 7.0 using 5M NaOH. The medium was then sterilized in autoclave at 121° C. for 20 minutes. A glucose solution was prepared separately, sterilized by filtration and then added to the standard medium only at the time of culture.

Several suppliers and concentrations of vegetable derived peptones and yeast extract were evaluated in the composition of the animal product-free culture medium described above.

Moreover, the influence of different pH's, range from 6.5 to 8.5, in the animal product-free culture medium (3% w/v NZ soy BL4, 3% w/v YE251 e 0.0625% w/v cysteine hydrochloride) was also investigated.

Example 2. *C. histolyticum* Growth in Animal Product-Free Culture Media and Standard Culture Medium, as Defined in Example 1

Initially, the frozen stock culture of *Clostridium histolyticum* (100 μL) was suspended in 1 mL of culture media (standard or animal product-free culture medium, as described in Example 1, and after, filled with the respective culture media to reach the 10 mL final volume (culture denominated as inoculum). Tubes containing the inoculum were incubated at 37° C., in anaerobiosis, for approximately 16 hours.

After this period, 3 mL of the inoculum were incubated in 250 mL flasks containing 150 mL of the respective *C. histolyticum* culture media. The culture was then maintained at 37° C. for 12-14 hours under anaerobic conditions ($N_2$ addition). All the analyses presented were carried out at the end of the 12-14 hours interval. Bacterial growth was determined through analysis of optical density—OD—using a spectrophotometer with a set wavelength of 600 nm.

FIG. 1 shows the OD (optical density) results for *C. histolyticum* (ATCC 21000) growth in animal product-free culture medium comprising vegetable derived peptone (3% w/v) and yeast extract (3% w/v) from different suppliers. The evaluated suppliers display similar results of bacterial growth. In FIG. 1 it is clearly observed a significant increase in the OD measured when animal product-free culture medium was used, indicating higher bacterial growth rate when compared to the standard medium (with animal derived peptones; Vetec+Casein). All animal product-free culture media represented in FIG. 1 contain 625 mg/L of cysteine hydrochloride and pH of approximately 7.0.

The growth rate of *C. histolyticum* when subjected to animal product-free culture medium with diverse concentrations of vegetable peptones (Hy-pep 1511; 1-3% w/v) and yeast extract (YE 251; 0-3% w/v) is presented in FIG. 2. All animal product-free culture media represented in FIG. 2 contain 625 mg/L of cysteine hydrochloride and pH of approximately 7.0. Some variation in the *C. histolyticum* growth rate is observed among these animal product-free culture media. However, the OD values reached are always superior to those obtained when culturing *C. histolyticum* in a standard medium (with animal derived peptone).

Figure 3:
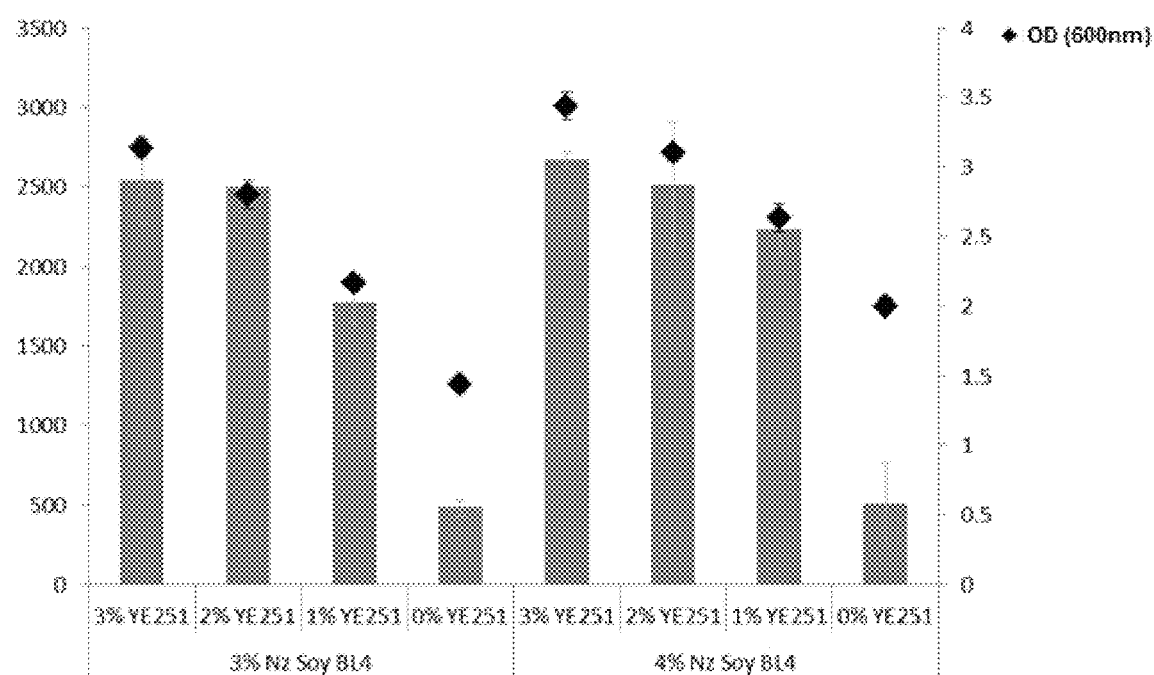
FIG. 3. Bacterial growth (OD) and enzymatic activity of *C. histolyticum* (ATCC 21000) animal product-free cultures with different concentrations of yeast extract (0-3% w/v), 3% w/v or 4% w/v of soy peptone and 0.0625% w/v of cysteine hydrochloride.

The importance of the yeast extract in the composition of the animal product-free culture medium is demonstrated in FIG. 3 (animal product-free culture media comprising 0, 1, 2 or 3% of yeast extract). It can be observed that the absence of yeast extract in the animal product-free culture medium inhibits the bacterial growth as well as collagenolytic and gelatinolytic protease production, even with an increase amount of vegetable peptone (3 and 4% w/v concentrations of vegetable derived peptone). All animal product-free culture media represented in FIG. 3 contain 625 mg/L of cysteine hydrochloride and pH of approximately 7.0. The evaluation of collagenolytic and gelatinolytic activity was carried out as described in Example 4.

Figure 4:
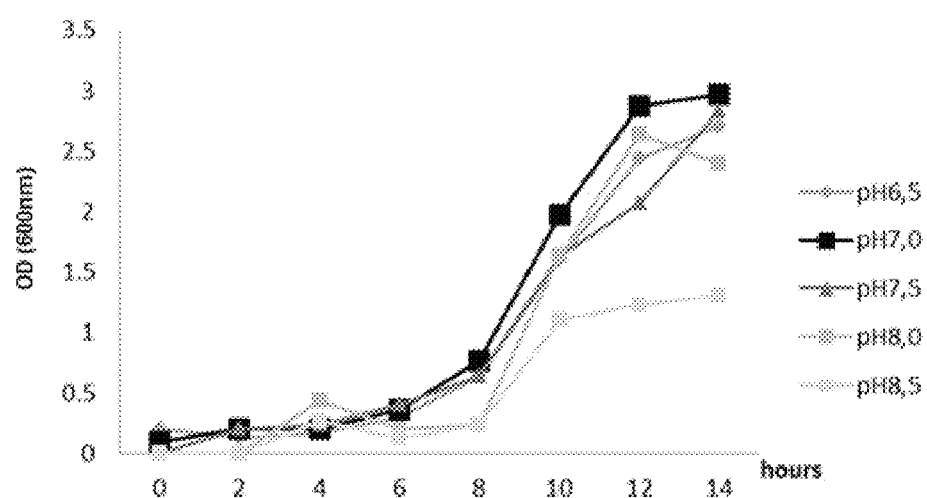
FIG. 4. pH influence on bacterial growth (optical density 600 nm) of *C. histolyticum* (ATCC 21000) in an animal product-free culture medium comprising 3% w/v of soy peptone (NZ Soy BL4), 3% w/v of yeast extract (YE251) and 0.0625% w/v of cysteine hydrochloride.
Figure 5:
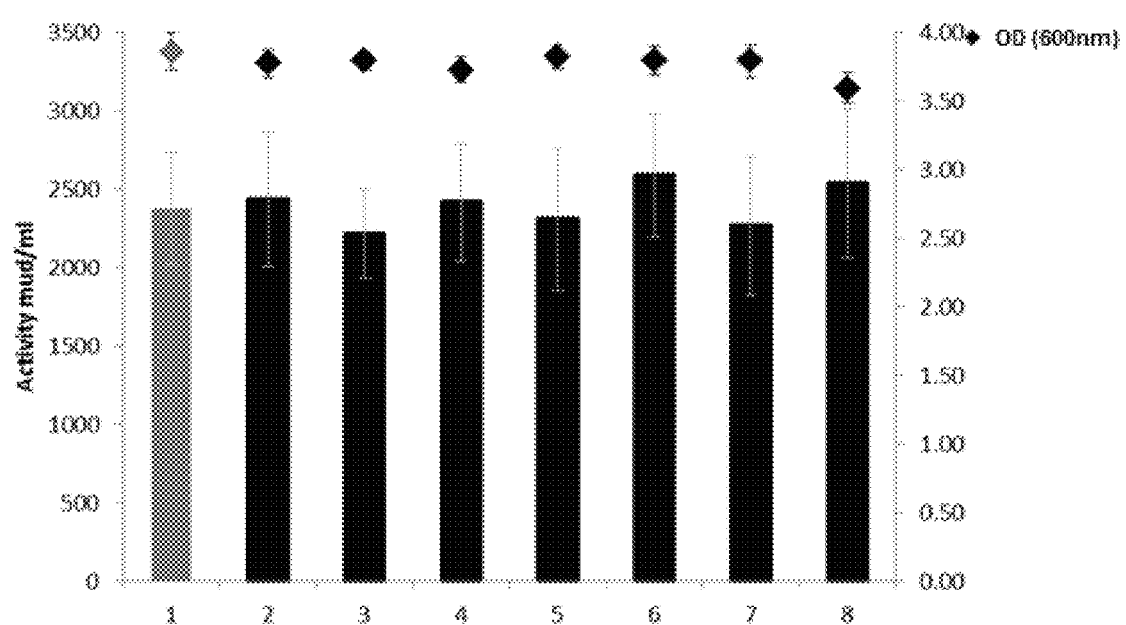
FIG. 5. Bacterial growth (OD) and enzymatic activity of *C. histolyticum* (ATCC 21000) cultures supplemented with inorganic salts, vitamins and amino acids. Culture media used are animal product-free and comprise: 3% w/v of soy peptone (NZ SOY BL4), 3% w/v of yeast extract (YE 251) and 0.0625% w/v of cysteine hydrochloride. The bars (1-8) in the chart refer to:
1—Control Medium (Ctrl):
  NZ-soy BL4 (3%);
  Yeast extract YE 251 (3%);
  Cysteine hydrochloride (0.0625%);
2—Ctrl+Salts*
3—Ctrl+Vitamins**
4—Ctrl+Vitamins**+Salts*
5—Ctrl+Aa***
6—Ctrl+Aa*+Vitamins
7—Ctrl+Aa***+Salts*
8—Ctrl+Aa*+Vitamins+Salts*

FIG. 4 represents the results of bacterial growth obtained of *C. histolyticum* in growth medium with pH ranging from 6.5 to 8.5. In the pH range evaluated, only the most basic pH (pH 8.5) negatively influenced the bacterial growth.

Example 3. Production of Animal Product-Free and Standard Culture Medium for Producing a Supernatant of *Clostridium histolyticum* Comprising Collagenolytic and Gelatinolytic Proteases The standard (conventional) culture media were prepared according to Example 1.

The animal product-free culture medium of the present invention was prepared using the following ingredients (grams per liter): vegetable derived peptone (30 g); yeast extract (30 g); cysteine hydrochloride (0.625 g); arginine hydrochloride (3.75 g) and pH 7.0 (adjusted with 5M NaOH).

Experiments to demonstrate the surprising effect of the animal product-free culture medium for *C. histolyticum* described in the present invention were carried out with five different types of culture media, which comprise the following ingredients:

Medium 1: soy peptone (30 g; NZ-Soy BL4®); yeast extract (30 g; YE 251®); cysteine hydrochloride (0.625 g), pH 7.0 (adjusted with 5M NaOH).

Medium 2: soy peptone (30 g; NZ-Soy BL4®); yeast extract (30 g; YE 251®); cysteine hydrochloride (0.625 g), pH 7.0 (adjusted with 5M NaOH) and additional salts and/or, vitamins and/or amino acids (described in FIG. 5).

Medium 3: soy peptone (30 g; NZ-Soy BL4®); yeast extract (30 g; YE 251®); cysteine hydrochloride (0.625 g), pH 7.0 (adjusted with 5M NaOH) and additional amino acids (Groups 1 to 6, described in FIG. 9).

Medium 4: soy peptone (30 g; NZ-Soy BL4®); yeast extract (30 g; YE 251®); cysteine hydrochloride (0.625 g), pH 7.0 (adjusted with 5M NaOH) and additionally glycine and/or arginine.

Medium 5: soy peptone (30 g; NZ-Soy BL4®); yeast extract (30 g; YE 251®); cysteine hydrochloride (0.625 g); arginine hydrochloride (3.75 g), pH 7.0 (adjusted with 5M NaOH) and additional inorganic salts and vitamins (described in FIG. 6).

Different vegetable derived peptones suppliers were evaluated to *C. histolyticum* collagenolytic and gelatinolytic proteases production, showing similar results to NZ-Soy BL4®. In the same way, different yeast extracts suppliers showed similar results to those obtained with YE 251® used in the animal product-free culture media.

The vegetable derived peptones and yeast extracts suitable to provide the animal product-free culture medium are not limited to the ones used in the examples of the present invention. Vegetable peptones and yeast extracts that demonstrate good solubility in water can be used in the preparation of the culture medium for *C. histolyticum* according to the present invention, since they are animal product-free.

After solubilizing all components of the animal product-free culture medium in water, as described above, and adjusting the pH to 7.0 (5M NaOH), the culture medium was sterilized in autoclave at 121° C. for 20 minutes.

Example 4. Production of a Supernatant of
*Clostridium histolyticum* Liquid Culture
Comprising One or More Collagenolytic and
Gelatinolytic Proteases in the Animal Product-Free
Culture Medium Defined in Example 3 and
Standard Culture Medium Defined in Example 1

*C. histolyticum* culture in an animal product-free culture medium was carried out as described in Example 2. The culture media evaluated are described in Example 3 (media 1 to 5).

After 12-14 hours of *C. histolyticum* culture in the animal product-free culture media described in Example 3, the bacteria cells were centrifuged and the collagenolytic and gelatinolytic activity of the proteases from the culture supernatant was quantified. Eight milliliters (8 mL) of the bacterial cultures were centrifuged at 500 rpm for 30 minutes at 4° C. for the removal of insoluble material (cells, cell debris, precipitate, among others).

The protein profile of the supernatant was evaluated by SDS PAGE 7.5% gel electrophoresis (7.5%) under non-reducing conditions (silver stained). The enzymatic activity profile (non-specific) was evaluated through SDS-PAGE gel electrophoresis comprising 10% of gelatin and stained with Coomassie blue (zymography). Both methodologies are broadly known by those skilled in the art.

The collagenolytic and gelatinolytic activity of the supernatants was quantified through EnzChek® Gelatinase/Collagenase Assay Kit (Molecular Probes, Invitrogen). Assays were carried out in microplates according to manufacturer instructions, using gelatin and/or collagen fluorescein conjugated as substrate. Fluorescence determinations were made using a fluorescence reader. Briefly, 100 µL of the centrifuged culture supernatant were mixed to the substrate diluted in the incubation buffer prepared according to the manufacturer instructions. Samples were incubated at 37° C. for 15 minutes and the fluorescence was determined at 515 nm wavelength using a fluorescence microplate reader. As a negative control, a sterile culture medium was used. As a positive control, it was used a Collagenase reagent provided with the kit and prepared according to manufacturer instructions.

Bacterial growth was determined by optical density—OD—using a spectrophotometer at 600 nm wavelength.

Initially, the animal product-free culture medium (medium 2; comprising vegetable peptone, yeast extract and cysteine) supplemented with vitamins, inorganic salts and amino acids was evaluated. This experiment demonstrated a small influence of these additives in cell growth as well as collagenolytic and gelatinolytic protease production by *Clostridium histolyticum* liquid culture (FIG. 5). Medium 1 was used as a control for this assay.

The addition of vitamins, inorganic salts and amino acids to the animal product-free culture medium described as medium 5 (comprising vegetable peptone, cysteine and arginine) also resulted in a small variation of the biomass (OD) and collagenolytic and gelatinolytic activity of the culture supernatant (FIG. 6), confirming that such vitamin and salt supplementation is optional to the culture medium of the present invention.

Figure 7:
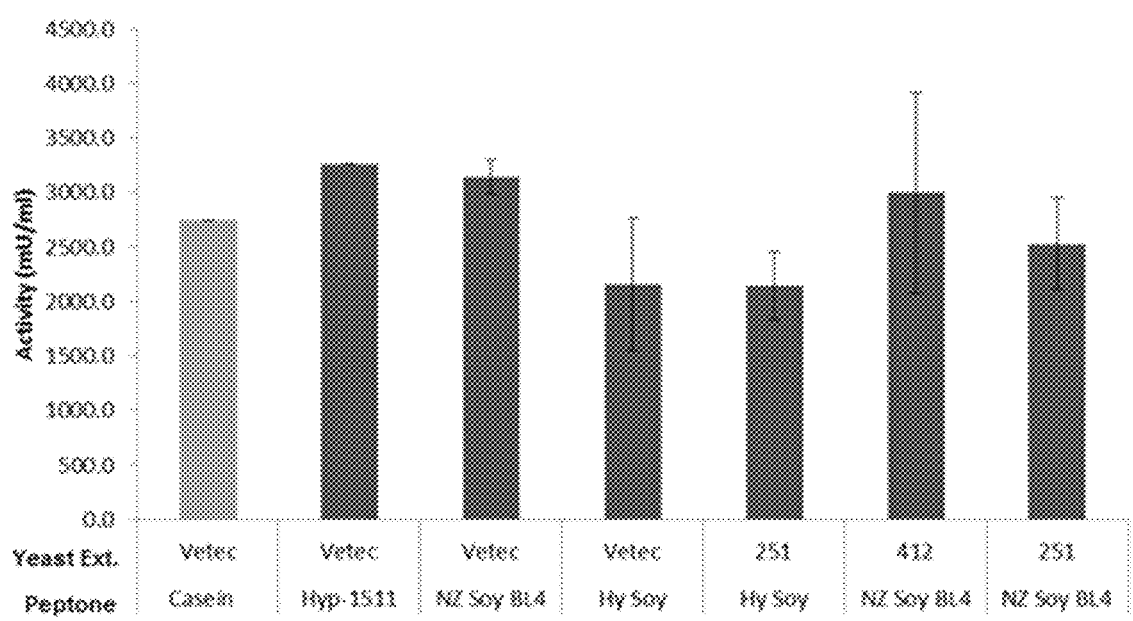

Qualitative variations (different suppliers) of the vegetable derived peptone and yeast extract components were also evaluated (Medium 1 comprising vegetable peptone, yeast extract and cysteine) regarding the collagenolytic and gelatinolytic supernatant production of a *C. histolyticum* culture. FIG. 7 shows that the results of collagenolytic and gelatinolytic activities obtained for these cultures are of the same magnitude as the results obtained for the *C. histolyticum* culture in standard medium (with animal peptone). Thus, there is a need of an additional ingredient to the culture medium in order to obtain increased collagenolytic and gelatinolytic activity in the supernatant of the *C. histolyticum* liquid culture, which has been solved by the present invention culture medium.

Surprisingly, animal product-free *C. histolyticum* culture with cysteine and arginine amino acids (culture medium 4) results in a supernatant with significantly higher collagenolytic and gelatinolytic activity than the supernatant obtained when using animal product-free culture medium containing only the amino acid cysteine (Medium 1, used as a control of this assay; FIG. 8). Such effect is due to arginine since the addition of another amino acid, for instance glycine, leads to reduction of collagenolytic and gelatinolytic activity observed.

FIG. 9 shows results of collagenolytic and gelatinolytic activity and OD (600 nm) observed in *C. histolyticum* culture in medium 3 (animal product-free culture medium comprising cysteine and amino acid groups). As a control, a culture using medium 1 was carried out (animal product-free culture medium containing only the amino acid cysteine). It can be observed that no amino acid or amino acid combination added to the culture medium other than cysteine and arginine was able to increase collagenolytic and gelatinolytic activity in the supernatant of *C. histolyticum* liquid culture (FIG. 8).

Additionally, it can be observed that 14 hours of fermentation are enough to obtain the collagenolytic and gelatinolytic enzymes in suitable levels for industrial production. This is a shorter culture process when compared with the ones generally applied, an industrial advantage of the process described in the present invention.

Example 5. Production of a Supernatant of
*Clostridium histolyticum* Liquid Culture
Comprising One or More Collagenolytic and
Gelatinolytic Proteases in Animal Product-Free
Culture Medium—Bioreactor Culture Initially, the frozen stock culture of *Clostridium histolyticum* (100 µL) was suspended in 1 mL of animal product-free culture medium (medium 1, as defined below), and then filler with the respective culture medium to the final volume of 10 mL (culture denominated as pre-inoculum). Tubes containing the pre-inoculums were incubated at 37° C. under anaerobic conditions for approximately 16 hours. After this period, 3 mL of the aforesaid pre-inoculum was then incubated in 250 mL flasks containing 150 mL of the respective *C. histolyticum* culture medium. This was denominated inoculum, and it was maintained at 37° C. during 12-14 hours under anaerobic conditions (attained through the addition of nitrogen gas).

60 mL of the inoculum were transferred to 3 L of *C. histolyticum* culture medium in a bioreactor (New Brunswick) and cultured at 37° C. under anaerobic conditions (nitrogen gas addition). The pH was monitored and controlled during the entire fermentation process being maintained in a range of 6.5 and 8.0. Such maintenance was achieved through the addition of 5M $NH_4OH$ or 2M $H_2SO_4$. The culture was maintained for about 14 hours, period in which culture has reached its stationary growth phase for at least 2 hours.

Two culture media were evaluated, and their composition is as described below (grams per liter):

Medium 1: soy peptone (30 g; NZ-Soy BL4®); yeast extract (30 g YE 251®); cysteine hydrochloride (0.625 g) and pH 7.0 (adjusted with 5 M NH$_4$OH after sterilization).

Medium 6: soy peptone (30 g; NZ-Soy BL4®); yeast extract (30 g YE 251®); cysteine hydrochloride (0.625 g), arginine hydrochloride (3.75 g) and pH 7.0 (adjusted with 5 M NH$_4$OH after sterilization).

The process for obtaining a *C. histolyticum* culture supernatant with collagenolytic and gelatinolytic activities according to the present invention is detailed below.

1—Cell bank preparation: a cell bank was prepared using isolated ATCC 21000 colonies from agar plates (a culture medium of: soy peptone, yeast extract and agar). Colonies with apparent higher cell growth were isolated and inoculated in a liquid cell bank medium containing the same ingredients as the solid medium, with the exception of agar. In order to preserve the cells during freeze and thaw, thus maintaining its viability, 10% sterile glycerol was added to the *C. histolyticum* liquid culture. This liquid culture was then fractionated into cryotubes and frozen at −80° C. for future use, such conditions allows the stock cultures to be used for at least 1 year without losing cell viability.

2—Growth phase (pre-inoculum and inoculum preparation): a cell bank aliquot was rapidly thawed at room temperature; a 100 μL aliquot was transferred to 1 mL of an animal product-free culture medium (Medium 1), to which 9 mL of the same medium was added for bacterial growth at 37° C. under anaerobic conditions for about 16 hours (pre-inoculum). Subsequently, the pre-inoculum was used to generate the inoculum as described previously.

3—Fermentation phase (production of supernatant of *C. histolyticum* liquid culture comprising collagenolytic and gelatinolytic proteases): 60 mL of the inoculum were transferred to a bioreactor containing 3 L of animal product-free culture medium (pH 7.0, Medium 1) and maintained at 37° C. for about 14 hours under anaerobic conditions (addition of nitrogen gas). During the culture, the pH was controlled by the addition of 5M $NH_4OH$ when the pH reached values lower than 6.5, or 2M$H_2SO_4$ when the pH reached values higher than 8.0.

The maximum bacterial growth rate and collagenolytic and gelatinolytic proteases production occurred after 14 hours of bacterial fermentation (FIG. 10).

The same process was carried out using Medium 6 as animal product-free culture medium described at step 3.

Bacterial growth was monitored in intervals of 2 hours through optical density measurements (600 nm) which were performed using a spectrophotometer.

The protein and enzymatic supernatant profile obtained from the *C. histolyticum* cultures described above were evaluated through SDS PAGE gel electrophoresis (7.5%) under non-reducing conditions and stained with silver nitrate (FIG. 11) and non-reducing SDS-PAGE gel comprising 10% gelatin and stained with Coomassie blue (FIGS. 10 and 11; zymography).

4—Supernatant of *C. histolyticum* liquid culture production and recovery of collagenolytic and gelatinolytic proteases: In order to obtain the liquid culture supernatant and recover the collagenolytic and gelatinolytic enzymes, the procedures described in Example 4 (centrifugation) or Example 6 (saline precipitation followed by dialysis and lyophilization) were performed or tangential flow filtration (5 KDa pore size) followed by lyophilization as presented below (Example 7). The collagenolytic and gelatinolytic activities of the supernatant were monitored through fluorimetric assays according to the detailed description presented in Example 4 (FIGS. 10 and 11).

The results (OD, enzymatic activity and zymography) of two fermentative processes carried out in culture Medium 1 (Medium 1) are demonstrated in FIG. 10.

FIG. 11 shows the results (OD, enzymatic activity, SDS-PAGE gel/silver stained and zymography) of a fermentative process carried out in Medium 6. It can be observed in FIG. 11, a bacterial growth curve similar to that obtained when the fermentation took place in a bioreactor using medium 1 (comprising cysteine only, FIG. 10). However and surprisingly, it can also be observed a significantly higher collagenolytic and gelatinolytic activity, showing that the addition of arginine to the animal product-free culture medium influences the increase of collagenolytic and gelatinolytic enzymes production in *C. histolyticum* cultures (activity in U/mL).

FIG. 12 shows the comparison of collagenolytic and gelatinolytic activity (mU/mL) and optical density (OD 600 nm) between cultures with Medium 1 (containing only amino acid cysteine) and with Medium 6 (containing cysteine and arginine), clearly showing an average increase of 30% in the collagenolytic and gelatinolytic activity of the culture supernatant. Additionally, the predominance of high molecular weight proteins, identified here as being collagenases, in the SDS-PAGE gels (silver stained and zymography, FIGS. 10 and 11), demonstrate the quality of the supernatants obtained from the *C. histolyticum* cultures of the present invention.

Example 6. Recovery of Collagenolytic and Gelatinolytic Proteases from a *C. histolyticum* Liquid Culture Supernatant in an Animal Product-Free Culture Medium The supernatant comprising the collagenolytic and gelatinolytic proteases was obtained through *C. histolyticum* culture according to Example 5, using Medium 6 (comprising cysteine and arginine) in step 3.

In order to recover the collagenolytic and gelatinolytic proteases from *C. histolyticum* liquid culture supernatant, 243.73 g of $(NH_4)_2SO_4$ was added to 500 mL of supernatant, the mixture was then shaken and stored in a freezer for 2 h (saline precipitation stage). Subsequently, the mixture was centrifuged at a speed of 8500 rpm for 30 min at 4° C. The material, obtained after the saline precipitation and centrifugation, was resuspended in 12.0 mL of 2 mM sodium phosphate buffer, pH 7.2, and then submitted to dialysis with 2 mM sodium phosphate buffer, pH 7.2. Before freezing and lyophilization, the samples were submitted to three buffer exchange. Lyophilization was carried out for at least 18 h. The lyophilized material was then collected for analysis and characterization via 7.5% SDS-PAGE gel electrophoresis under non-reducing conditions and silver staining (FIG. 13). The excellent quality and high stability of the supernatant and proteases obtained from *C. histolyticum* culture according to the present invention are demonstrated by the results from SDS-PAGE analysis, which shows a predominant presence of high molecular weight proteins (collagenases), which prevalence is increased after lyophilization (recovery of 90% of the initial supernatant enzymatic activity).

Example 7. Pharmaceutical Composition for Topical Use Comprising *C. histolyticum* Collagenases—Stability Assays The pharmaceutical composition used to exemplify the present invention was a dermatological ointment comprising:

| Ingredient | Quantity/g | | |
|---|---|---|---|
| | Formulation 1 | Formulation 2 | Formulation 3 |
| Collagenase | 0.2 U | 0.6 U | 1.8 U |
| Liquid vaseline - mineral oil | 0.0188 mL | 0.0188 mL | 0.0188 mL |
| Solid vaseline - MBK | 0.9846 g | 0.9846 g | 0.9846 g |

The specific collagenase activity was determined by enzymatic hydrolysis of a synthetic substrate (Carbobenzoxy-Gly-Pro-Gly-Gly-Pro-Ala), through colorimetric ninhydrin assay. An enzyme unit is defined as being responsible for the release of 1 μmol of Gly-Pro-Ala from Z-Gly-Pro-Gly-Gly-Pro-Ala hexapeptide in 1 minute at 37° C.

The pharmaceutical composition was prepared through the dispersion and homogenization of the lyophilized component (equivalent amount of the specific collagenase activity equal to 0.2 U, 0.6 U and 1.8 U/g of formulation), obtained according to Example 5 (lyophilized component of the supernatant obtained through a culture using Medium 6 after tangential flow filtration), in the other excipients. The 0.6 U/g dose is considered a therapeutic dose proper for human use.

The stability study was carried out with formulation 2 described above, stored in aluminum tubes containing 30 g. The performed tests, specification and observed results are described in Tables 3 and 4. All tests were performed in stability chambers.

*Clostridium histolyticum* liquid culture described in the present invention (Medium 6, comprising cysteine and arginine).

Example 8. Pharmaceutical Composition for Topical Use Comprising *C. histolyticum* Collagenases—Toxicity The pharmaceutical compositions used to exemplify the present invention are the same used to perform the stability assays described above (Example 7).

A repeated dose dermal toxicity test was performed (21 days) on rats scarified skin with the pharmaceutical compositions according to Example 7 (active ingredient: lyophilized with specific Collagenase activity of 0.2 U/g, 0.6 U/g and 1.8 U/g). As a test control, it was used a placebo composition, prepared according to Example 7, however, without adding the active ingredient.

The test, based on the OECD 410 Guideline, consisted of surgically provoking an injury using a 4 mm sterile punch at the center of the dorsal median line on the first day of application (dorsal area hair removed by an epilator device). The topical application of the composition (0.425 g; compositions containing 0.2 U/g, 0.6 U/g and 1.8 U/g of collagenase) was done once-a-day for 21 days with a spatula, in an area equivalent to 30-40 $cm^2$ inside and around the injury. This was performed in three groups of *Rattus norvegicus* (albine variety, Wistar strain), each group with 10 rats, 5 males and 5 nulliparous and non-pregnant females.

The application site was preserved with gauze and a non-irritating tape for about 24 hours after the application.

TABLE 3

Long term stability: 30° C. ± 2° C., 75% ± 5% RH (Relative Humidity).

| | | ANALYSIS PERIODS | | |
|---|---|---|---|---|
| TEST | SPECIFICATION | INITIAL | 3 months | 6 months |
| ASPECT | SOFT OINTMENT FREE FROM FOREIGN PARTICLES AND LUMPS | IN ACCORDANCE | IN ACCORDANCE | IN ACCORDANCE |
| COLOR | WHITE TO LIGHT BROWN | IN ACCORDANCE | IN ACCORDANCE | IN ACCORDANCE |
| ODOR | DISTINCTIVE | IN ACCORDANCE | IN ACCORDANCE | IN ACCORDANCE |
| COLLAGENASE CONTENT | BETWEEN 90.0-120.0% 0.54-0.72 U/g | 106.5% 0.64 U/g | 103.3% 0.62 U/g | 107.4% 0.64 U/g |

TABLE 4

Accelerated stability: 40° C. ± 2° C., 75% ± 5% RH (Relative Humidity).

| | | ANALYSIS PERIODS | | |
|---|---|---|---|---|
| TEST | SPECIFICATION | INITIAL | 3 months | 6 months |
| ASPECT | SOFT OINTMENT FREE FROM FOREIGN PARTICLES AND LUMPS | IN ACCORDANCE | IN ACCORDANCE | IN ACCORDANCE |
| COLOR | WHITE TO LIGHT BROWN | IN ACCORDANCE | IN ACCORDANCE | IN ACCORDANCE |
| ODOR | DISTINCTIVE | IN ACCORDANCE | IN ACCORDANCE | IN ACCORDANCE |
| COLLAGENASE CONTENT | BETWEEN 90.0-120.0% 0.54-0.72 U/g | 106.5% 0.64 U/g | 104.5% 0.63 U/g | 109% 0.65 U/g |

Maintenance of the initial product characteristics is observed in both evaluated conditions, confirming the quality of the product obtained from the supernatant of In parallel, a placebo was applied (Collagenase Placebo) to a control group composed of 10 rats, 5 males and 5 females. Additionally, two satellite groups were formed (each group contains 10 rats, 5 males and 5 females), one evaluated with the highest dose (1.8 U/g) of the test composition and another with the control composition (Collagenase Placebo). They were also treated for 21 days and monitored for 14 days after the final period of exposure, with the intent of verifying reversibility, persistence or late effects of exposure to the test substance.

The following parameters were daily observed after each application:
1. Changes in hair and skin.
2. Changes in the eyes and mucous membranes.
3. Changes in breathing and circulation.
4. Changes in the Autonomous and Central Nervous System.
5. Changes in somatic-motor activity and standard behavior.
6. Other changes like trembling, seizure, salivation, diarrhea, lethargy, sleepiness and coma.

The weight (Table 5) and water and food intake were recorded weekly. At the end of the study, blood samples were collected for hematological analysis (hematocrit, hemoglobin concentration, erythrocytes count, red blood cell indexes calculation, total and differential leukocyte, prothrombin time, activated partial thromboplastin time and platelets count—Table 6) and biochemical (sodium, potassium, calcium, phosphorus, triglycerides, albumin, creatinine, urea, total protein, alanine and aspartate aminotransferases, cholesterol, and glycemia—Table 7). Later, the animals were submitted to euthanasia and necropsy (Table 8). Tissue samples were forwarded to histopathological analysis.

The application of repeated doses (21 days) of the described pharmaceutical composition, in all evaluated doses, did not induce death or changes in clinical parameters such as body weight, food and water intake, hematological, biochemical and/or anatomopathological parameters. Thus, the obtained results demonstrated that the dermal application of the pharmaceutical composition comprising the lyophilized component (0.2 U, 0.6 U and 1.8 U/g formulation) obtained according to Example 5 (lyophilized component obtained from *C. histolyticum* supernatant after tangential flow filtration procedure) over a period of 21 days was well tolerated and did not provoke changes possibly related to toxicity in *Rattus novergicus*. It was surprisingly observed that even with a therapeutic dose three-times higher than that considered for humans, the composition described in the present invention does not show signs of toxicity in rats.

TABLE 5

Body weight (male and female rats). Repeated dose dermal toxicity test (21 days) on rats of topical compositions comprising purified and lyophilized supernatant of *C. histolyticum* culture (ATCC 21000) using an animal product-free culture medium comprising soy peptone (30 g/L), yeast extract (30 g/L), cysteine hydrochloride (0.625 g/L) and arginine hydrochloride (3.75 g/L). Control composition: only with excipients.

| | Groups- males | | | | | | | | |
|---|---|---|---|---|---|---|---|---|---|
| | 0.2 U/g | | | 0.6 U/g | | | 1.8 U/g | | |
| WEEKS | MEAN | S.D | n | MEAN | S.D. | n | MEAN | S.D. | n |
| 0 | 296.40 | 22.56 | 5 | 302.12 | 26.92 | 5 | 306.56 | 13.94 | 5 |
| 1 | 279.14 | 17.93 | 5 | 282.68 | 28.46 | 5 | 292.72 | 19.68 | 5 |
| 2 | 283.04 | 17.54 | 5 | 277.10 | 15.17 | 5 | 301.68 | 15.09 | 5 |
| 3 | 280.94 | 19.34 | 5 | 273.42 | 18.43 | 5 | 291.20 | 20.19 | 5 |
| 4 | | | | | | | | | |
| 5 | | | | | | | | | |

| | Groups - males | | | | | | | | |
|---|---|---|---|---|---|---|---|---|---|
| | Control | | | Satellite-Control | | | 1.8 U/g-Satellite | | |
| WEEKS | MEAN | S.D | n | MEAN | S.D. | n | MEAN | S.D. | n |
| 0 | 298.68 | 14.04 | 5 | 284.00 | 39.46 | 5 | 311.18 | 18.05 | 5 |
| 1 | 279.42 | 15.00 | 5 | 285.16 | 15.10 | 5 | 292.58 | 15.10 | 5 |
| 2 | 287.22 | 19.90 | 5 | 293.50 | 17.76 | 5 | 295.92 | 14.75 | 5 |
| 3 | 278.96 | 16.01 | 5 | 298.08 | 16.36 | 5 | 300.94 | 15.77 | 5 |
| 4 | | | | 328.12 | 9.95 | 5 | 335.12 | 21.56 | 5 |
| 5 | | | | 324.26 | 9.24 | 5 | 338.34 | 17.92 | 5 |

| | Groups -females | | | | | | | | |
|---|---|---|---|---|---|---|---|---|---|
| | 0.2 U/g | | | 0.6 U/g | | | 1.8 U/g | | |
| WEEKS | MEAN | S.D | n | MEAN | S.D. | n | MEAN | S.D. | n |
| 0 | 252.20 | 21.28 | 5 | 221.00 | 7.89 | 5 | 238.86 | 14.88 | 5 |
| 1 | 238.02 | 21.38 | 5 | 215.14 | 15.93 | 5 | 226.60 | 10.31 | 5 |
| 2 | 247.14 | 21.54 | 5 | 218.36 | 10.92 | 5 | 235.10 | 12.05 | 5 |
| 3 | 244.42 | 15.77 | 5 | 212.52 | 12.20 | 5 | 240.98 | 12.59 | 5 |
| 4 | | | | | | | | | |
| 5 | | | | | | | | | |

TABLE 5-continued

Body weight (male and female rats). Repeated dose dermal toxicity test (21 days) on rats of topical compositions comprising purified and lyophilized supernatant of *C. histolyticum* culture (ATCC 21000) using an animal product-free culture medium comprising soy peptone (30 g/L), yeast extract (30 g/L), cysteine hydrochloride (0.625 g/L) and arginine hydrochloride (3.75 g/L). Control composition: only with excipients.

| | Groups -females | | | | | | | | |
|---|---|---|---|---|---|---|---|---|---|
| | Control | | | Satellite-Control | | | 1.8 U/g-Satellite | | |
| WEEKS | MEAN | S.D | n | MEAN | S.D. | n | MEAN | S.D. | n |
| 0 | 230.56 | 19.88 | 5 | 252.72 | 32.44 | 5 | 234.16 | 8.57 | 5 |
| 1 | 223.60 | 9.98 | 5 | 228.32 | 11.05 | 5 | 226.70 | 9.75 | 5 |
| 2 | 235.72 | 15.04 | 5 | 238.44 | 7.61 | 5 | 227.64 | 8.16 | 5 |
| 3 | 225.42 | 13.91 | 5 | 247.70 | 15.98 | 5 | 242.98 | 11.99 | 5 |
| 4 | | | | 258.32 | 12.35 | 5 | 256.58 | 9.85 | 5 |
| 5 | | | | 247.16 | 6.91 | 5 | 247.12 | 7.71 | 5 |

TABLE 6

Hematological analysis (male and female rats). Repeated dose dermal toxicity test (21 days) on rats of 1 topical compositions comprising purified and lyophilized supernatant of *C. histolyticum* culture (ATCC 21000) using an animal product-free culture medium comprising soy peptone (30 g/L), yeast extract (30 g/L), cysteine hydrochloride (0.625 g/L) and arginine hydrochloride (3.75 g/L). Control composition: only with excipients.

| | Groups - males | | | | | | | | |
|---|---|---|---|---|---|---|---|---|---|
| | 0.2 U/g | | | 0.6 U/g | | | 1.8 U/g | | |
| | MEAN | S.D. | n | MEAN | S.D. | n | MEAN | S.D. | n |
| Erythrocyte mm$^3$ | 9.68 | 0.50 | 5 | 9.46 | 0.17 | 5 | 9.26 | 0.53 | 5 |
| Hematocrit % | 54.20 | 2.17 | 5 | 53.20 | 0.84 | 5 | 53.00 | 2.12 | 5 |
| Hemoglobin g/dL | 19.06 | 0.61 | 5 | 18.62 | 0.37 | 5 | 18.62 | 1.03 | 5 |
| MCV fL | 56.02 | 1.01 | 5 | 56.25 | 1.50 | 5 | 57.31 | 2.18 | 5 |
| MCH Pg | 19.71 | 0.60 | 5 | 19.69 | 0.64 | 5 | 20.11 | 0.32 | 5 |
| MCHC mg/dL | 35.18 | 0.69 | 5 | 35.00 | 0.74 | 5 | 35.12 | 0.93 | 5 |
| Leucocyte mm$^3$ | 6060.00 | 1145.86 | 5 | 6700.00 | 1208.30 | 5 | 6140.00 | 1335.29 | 5 |
| Segmented mm$^3$ | 2017.00 | 780.36 | 5 | 1910.00 | 661.28 | 5 | 1698.20 | 659.76 | 5 |
| Eosinophil mm$^3$ | 59.60 | 36.16 | 5 | 28.00 | 38.66 | 5 | 43.80 | 66.46 | 5 |
| Lymphocyte mm$^3$ | 3864.00 | 842.49 | 5 | 4651.80 | 711.06 | 5 | 4292.80 | 860.02 | 5 |
| Monocyte mm$^3$ | 119.40 | 38.86 | 5 | 125.60 | 56.70 | 5 | 105.20 | 76.67 | 5 |
| Platelets mm$^3$ | 1164600.0 | 111428.5 | 5 | 1276200.0 | 174246.1 | 5 | 1207800.0 | 207705.8 | 5 |
| P T Seg | 8.00 | 0.00 | 5 | 8.20 | 0.45 | 5 | 8.60 | 0.55 | 5 |
| Pa T T Seg | 29.80 | 1.10 | 5 | 30.20 | 0.84 | 5 | 30.40 | 1.14 | 5 |

| | Groups - males | | | | | | | | |
|---|---|---|---|---|---|---|---|---|---|
| | Control | | | Satellite-Control | | | 1.8 U/g-Satellite | | |
| | MEAN | S.D. | n | MEAN | S.D. | n | MEAN | S.D. | n |
| Erythrocyte mm$^3$ | 9.32 | 0.26 | 5 | 9.34 | 0.34 | 5 | 9.30 | 0.20 | 5 |
| Hematocrit % | 51.60 | 1.52 | 5 | 51.40 | 2.61 | 5 | 52.00 | 2.74 | 5 |
| Hemoglobin g/dL | 17.88 | 0.55 | 5 | 18.30 | 0.62 | 5 | 18.26 | 1.04 | 5 |
| MCV fL | 55.38 | 1.39 | 5 | 55.03 | 1.80 | 5 | 55.89 | 2.00 | 5 |
| MCH Pg | 19.18 | 0.26 | 5 | 19.60 | 0.45 | 5 | 19.62 | 0.74 | 5 |
| MCHC mg/dL | 34.66 | 0.72 | 5 | 35.63 | 0.70 | 5 | 35.12 | 0.70 | 5 |
| Leucocyte mm$^3$ | 5900.00 | 1449.14 | 5 | 5520.00 | 884.31 | 5 | 6360.00 | 1099.09 | 5 |
| Segmented mm$^3$ | 1824.20 | 986.49 | 5 | 1262.80 | 408.65 | 5 | 1712.40 | 659.01 | 5 |
| Eosinophil mm$^3$ | 38.00 | 36.99 | 5 | 61.80 | 48.48 | 5 | 28.40 | 39.12 | 5 |

TABLE 6-continued

Hematological analysis (male and female rats). Repeated dose dermal toxicity test (21 days) on rats of 1 topical compositions comprising purified and lyophilized supernatant of *C. histolyticum* culture (ATCC 21000) using an animal product-free culture medium comprising soy peptone (30 g/L), yeast extract (30 g/L), cysteine hydrochloride (0.625 g/L) and arginine hydrochloride (3.75 g/L). Control composition: only with excipients.

|  | | | | | | | | | |
|---|---|---|---|---|---|---|---|---|---|
| Lymphocyte mm³ | 3946.60 | 661.89 | 5 | 4139.20 | 731.73 | 5 | 4593.20 | 1082.69 | 5 |
| Monocyte mm³ | 91.20 | 30.55 | 5 | 77.00 | 30.67 | 5 | 26.00 | 36.60 | 5 |
| Platelets mm³ | 1078000.0 | 112712.0 | 5 | 983400.0 | 91971.73 | 5 | 1142600.0 | 210515.6 | 5 |
| P T Seg | 8.00 | 0.00 | 4 | 8.00 | 0.00 | 5 | 8.60 | 0.55 | 5 |
| Pa T T Seg | 29.50 | 0.58 | 4 | 28.20 | 1.30 | 5 | 28.60 | 1.14 | 5 |

| | Groups - females | | | | | | | | |
|---|---|---|---|---|---|---|---|---|---|
| | 0.2 U/g | | | 0.6 U/g | | | 1.8 U/g | | |
| | MEAN | S.D. | n | MEAN | S.D. | n | MEAN | S.D. | n |
| Erythrocyte mm³ | 8.14 | 0.46 | 5 | 8.32 | 0.55 | 5 | 7.80 | 0.42 | 5 |
| Hematocrit % | 49.00 | 1.41 | 5 | 49.40 | 2.70 | 5 | 47.00 | 1.22 | 5 |
| Hemoglobin g/dL | 17.10 | 0.66 | 5 | 16.80 | 0.93 | 5 | 16.18 | 0.76 | 5 |
| MCV fL | 60.28 | 1.86 | 5 | 59.44 | 2.32 | 5 | 60.39 | 3.44 | 5 |
| MCH Pg | 21.04 | 0.98 | 5 | 20.21 | 0.50 | 5 | 20.77 | 0.93 | 5 |
| MCHC mg/dL | 34.90 | 0.94 | 5 | 34.02 | 0.86 | 5 | 34.42 | 1.28 | 5 |
| Leucocyte mm³ | 4860.00 | 1062.07 | 5 | 4880.00 | 846.76 | 5 | 5020.00 | 1551.45 | 5 |
| Segmented mm³ | 1364.80 | 402.06 | 5 | 1123.00 | 332.24 | 5 | 1328.00 | 437.38 | 5 |
| Eosinophil mm³ | 52.20 | 45.37 | 5 | 12.40 | 27.73 | 5 | 9.40 | 21.02 | 5 |
| Lymphocyte mm³ | 3382.00 | 693.01 | 5 | 3659.00 | 646.94 | 5 | 3625.80 | 1134.61 | 5 |
| Monocyte mm³ | 61.00 | 36.01 | 5 | 85.60 | 34.67 | 5 | 56.80 | 13.22 | 5 |
| Platelets mm³ | 1132400 | 222246.0 | 5 | 1114600.0 | 91876.55 | 5 | 1011000.0 | 148403.2 | 5 |
| P T Seg | 8.40 | 0.89 | 5 | 8.00 | 0.00 | 5 | 8.40 | 0.89 | 5 |
| Pa T T Seg | 30.60 | 1.14 | 5 | 30.00 | 0.71 | 5 | 30.00 | 0.71 | 5 |

| | Groups - females | | | | | | | | |
|---|---|---|---|---|---|---|---|---|---|
| | Control | | | Satellite-Control | | | 1.8 U/g-Satellite | | |
| | MEAN | S.D. | n | MEAN | S.D. | n | MEAN | S.D. | n |
| Erythrocyte mm³ | 8.36 | 0.61 | 5 | 8.76 | 0.41 | 5 | 8.60 | 0.42 | 5 |
| Hematocrit % | 48.20 | 1.48 | 5 | 50.40 | 2.07 | 5 | 49.00 | 0.71 | 5 |
| Hemoglobin g/dL | 17.04 | 0.44 | 5 | 17.82 | 1.07 | 5 | 17.62 | 0.50 | 5 |
| MCV fL | 57.82 | 3.12 | 5 | 57.55 | 0.96 | 5 | 57.10 | 3.21 | 5 |
| MCH Pg | 20.45 | 1.31 | 5 | 20.33 | 0.43 | 5 | 20.54 | 1.35 | 5 |
| MCHC mg/dL | 35.36 | 0.71 | 5 | 35.34 | 1.04 | 5 | 35.96 | 0.85 | 5 |
| Leucocyte mm³ | 5180.0 | 1377.32 | 5 | 4440.00 | 1078.42 | 5 | 5280.00 | 1637.68 | 5 |
| Segmented mm³ | 1386.0 | 450.85 | 5 | 815.60 | 439.77 | 5 | 995.60 | 415.46 | 5 |
| Eosinophil mm³ | 27.60 | 26.14 | 5 | 65.20 | 67.48 | 5 | 43.00 | 29.01 | 5 |
| Lymphocyte mm³ | 3661.6 | 996.95 | 5 | 3497.20 | 783.17 | 5 | 4127.20 | 1452.48 | 5 |
| Monocyte mm³ | 104.8 | 95.46 | 5 | 62.00 | 44.32 | 5 | 114.20 | 71.51 | 5 |
| Platelets mm³ | 1050600 | 200655.9 | 5 | 1002000.0 | 86743.88 | 5 | 1028400.0 | 33080.21 | 5 |
| P T Seg | 8.20 | 0.45 | 5 | 8.20 | 0.84 | 5 | 8.40 | 0.55 | 5 |
| Pa T T Seg | 30.00 | 0.00 | 5 | 28.60 | 0.55 | 5 | 29.00 | 1.00 | 5 |

TABLE 7

Biochemical analysis (male and female rats). Repeated dose dermal toxicity test (21 days) on rats of topical compositions comprising purified and lyophilized supernatant of *C. histolyticum* culture (ATCC 21000) using an animal product-free culture medium comprising soy peptone (30 g/L), yeast extract (30 g/L), cysteine hydrochloride (0.625 g/L) and arginine hydrochloride (3.75 g/L). Control composition: only with excipients.

| | Groups - males | | | | | | | | |
|---|---|---|---|---|---|---|---|---|---|
| | 0.2 U/g | | | 0.6 U/g | | | 1.8 U/g | | |
| | MEAN | S.D. | n | MEAN | S.D. | n | MEAN | S.D. | n |
| Albumin g/dl | 4.58 | 0.13 | 5 | 4.46 | 0.15 | 5 | 4.60 | 0.25 | 5 |
| ALT U I/L | 67.86 | 8.03 | 5 | 58.92 | 5.05 | 5 | 62.00 | 8.86 | 5 |
| AST U I/L | 143.66 | 14.39 | 5 | 130.38 | 18.78 | 5 | 138.00 | 22.03 | 5 |
| Calcium mg/dl | 10.46 | 0.14 | 5 | 10.34 | 0.46 | 5 | 10.68 | 0.49 | 5 |
| Total Cholesterol mg/dl | 57.16 | 2.56 | 5 | 64.74 | 9.64 | 5 | 56.74 | 4.61 | 5 |
| Creatinine mg/dl | 0.36 | 0.05 | 5 | 0.32 | 0.08 | 5 | 0.36 | 0.05 | 5 |
| Phosphorus mg/dl | 7.84 | 0.65 | 5 | 7.44 | 0.54 | 5 | 8.30 | 0.80 | 5 |
| Glucose mg/dl | 96.00 | 9.43 | 5 | 97.60 | 12.18 | 5 | 93.60 | 11.28 | 5 |
| Potassium mEq/L | 6.20 | 0.66 | 5 | 5.24 | 0.49 | 5 | 5.88 | 0.63 | 5 |
| Total Proteins g/dl | 5.80 | 0.19 | 5 | 5.74 | 0.23 | 5 | 5.90 | 0.19 | 5 |
| Sodium mEq/L | 141.40 | 3.36 | 5 | 142.60 | 0.89 | 5 | 141.20 | 3.35 | 5 |
| Triglycerides mg/dl | 39.04 | 5.66 | 5 | 35.86 | 6.34 | 5 | 34.78 | 6.36 | 5 |
| Urea mg/dl | 57.62 | 8.41 | 5 | 60.16 | 7.49 | 5 | 58.56 | 1.78 | 5 |

| | Groups - males | | | | | | | | |
|---|---|---|---|---|---|---|---|---|---|
| | Control | | | Satellite-Control | | | 1.8 U/g-Satellite | | |
| | MEAN | S.D. | n | MEAN | S.D. | n | MEAN | D.P. | n |
| Albumin g/dl | 4.46 | 0.13 | 5 | 4.70 | 0.16 | 5 | 4.72 | 0.22 | 5 |
| ALT U I/L | 63.80 | 16.36 | 5 | 53.36 | 9.38 | 5 | 54.14 | 13.51 | 5 |
| AST U I/L | 155.12 | 18.16 | 5 | 115.00 | 16.16 | 5 | 112.18 | 30.71 | 5 |
| Calcium mg/dl | 10.38 | 0.29 | 5 | 10.70 | 0.57 | 5 | 10.68 | 0.25 | 5 |
| Total Cholesterol mg/dl | 61.72 | 7.43 | 5 | 59.52 | 6.40 | 5 | 69.50 | 14.49 | 5 |
| Creatinine mg/dl | 0.38 | 0.04 | 5 | 0.42 | 0.04 | 5 | 0.36 | 0.05 | 5 |
| Phosphorus mg/dl | 8.22 | 0.72 | 5 | 7.54 | 0.77 | 5 | 7.88 | 0.69 | 5 |
| Glucose mg/dl | 88.20 | 8.29 | 5 | 106.80 | 24.24 | 5 | 104.20 | 7.89 | 5 |
| Potassium mEq/L | 7.00 | 1.14 | 5 | 6.12 | 0.29 | 5 | 6.32 | 0.32 | 5 |
| Total Proteins g/dl | 5.66 | 0.30 | 5 | 6.30 | 0.16 | 5 | 6.42 | 0.33 | 5 |
| Sodium mEq/L | 158.00 | 27.40 | 5 | 142.60 | 1.14 | 5 | 141.60 | 1.82 | 5 |
| Triglycerides mg/dl | 43.30 | 7.58 | 5 | 57.66 | 9.18 | 5 | 67.49 | 46.41 | 5 |
| Urea mg/dl | 60.86 | 2.29 | 5 | 56.58 | 6.25 | 5 | 56.20 | 4.26 | 5 |

| | Groups - females | | | | | | | | |
|---|---|---|---|---|---|---|---|---|---|
| | 0.2 U/g | | | 0.6 U/g | | | 1.8 U/g | | |
| | MEAN | S.D. | n | MEAN | S.D. | n | MEAN | S.D. | n |
| Albumin g/dl | 4.70 | 0.17 | 5 | 4.44 | 0.17 | 5 | 4.64 | 0.11 | 5 |
| ALT U I/L | 66.46 | 15.07 | 5 | 69.38 | 14.48 | 5 | 61.56 | 8.22 | 5 |
| AST U I/L | 150.92 | 17.67 | 5 | 184.06 | 50.29 | 5 | 158.72 | 26.90 | 5 |
| Calcium mg/dl | 10.80 | 0.71 | 5 | 10.32 | 0.43 | 5 | 10.62 | 0.35 | 5 |
| Total Cholesterol mg/dl | 53.68 | 11.37 | 5 | 47.74 | 8.86 | 5 | 48.32 | 8.44 | 5 |
| Creatinine mg/dl | 0.38 | 0.08 | 5 | 0.42 | 0.08 | 5 | 0.30 | 0.07 | 5 |
| Phosphorus mg/dl | 7.66 | 1.28 | 5 | 8.24 | 1.75 | 5 | 8.06 | 1.85 | 5 |
| Glucose mg/dl | 90.80 | 12.38 | 5 | 93.60 | 12.05 | 5 | 95.20 | 20.03 | 5 |
| Potassium mEq/L | 6.04 | 0.87 | 5 | 6.08 | 1.26 | 5 | 7.20 | 2.07 | 5 |
| Total Proteins g/dl | 6.02 | 0.19 | 5 | 5.90 | 0.07 | 5 | 5.96 | 0.13 | 5 |
| Sodium mEq/L | 154.40 | 25.52 | 5 | 142.20 | 1.30 | 5 | 166.40 | 29.07 | 5 |
| Triglycerides mg/dl | 39.34 | 7.38 | 5 | 33.08 | 3.88 | 5 | 44.84 | 13.32 | 5 |
| Urea mg/dl | 57.42 | 3.85 | 5 | 63.54 | 7.95 | 5 | 57.02 | 12.79 | 5 |

TABLE 7-continued

Biochemical analysis (male and female rats). Repeated dose dermal toxicity test (21 days) on rats of topical compositions comprising purified and lyophilized supernatant of *C. histolyticum* culture (ATCC 21000) using an animal product-free culture medium comprising soy peptone (30 g/L), yeast extract (30 g/L), cysteine hydrochloride (0.625 g/L) and arginine hydrochloride (3.75 g/L). Control composition: only with excipients.

| | Groups - females | | | | | | | | |
|---|---|---|---|---|---|---|---|---|---|
| | Control | | | Satellite-Control | | | 1.8 U/g-Satellite | | |
| | MEAN | S.D. | n | MEAN | S.D. | n | MEAN | S.D. | n |
| Albumin g/dl | 4.54 | 0.15 | 5 | 5.04 | 0.29 | 5 | 4.84 | 0.18 | 5 |
| ALT U I/L | 49.04 | 9.68 | 5 | 37.38 | 5.90 | 5 | 41.88 | 15.63 | 5 |
| AST U I/L | 173.02 | 28.78 | 5 | 97.82 | 9.16 | 5 | 124.84 | 17.31 | 5 |
| Calcium mg/dl | 10.33 | 0.34 | 5 | 10.64 | 0.25 | 5 | 10.64 | 0.21 | 5 |
| Total Cholesterol mg/dl | 39.74 | 3.50 | 5 | 43.70 | 14.02 | 5 | 36.15 | 7.24 | 5 |
| Creatinine mg/dl | 0.36 | 0.05 | 5 | 0.44 | 0.09 | 5 | 0.42 | 0.04 | 5 |
| Phosphorus mg/dl | 7.70 | 0.84 | 5 | 6.06 | 0.30 | 5 | 7.16 | 0.48 | 5 |
| Glucose mg/dl | 89.80 | 13.29 | 5 | 110.40 | 13.46 | 5 | 100.40 | 15.50 | 5 |
| Potassium mEq/L | 5.92 | 0.33 | 5 | 5.60 | 0.35 | 5 | 6.18 | 0.46 | 5 |
| Total Proteins g/dl | 5.76 | 0.30 | 5 | 6.74 | 0.13 | 5 | 6.54 | 0.23 | 5 |
| Sodium mEq/L | 141.20 | 4.44 | 5 | 142.60 | 1.14 | 5 | 142.60 | 0.89 | 5 |
| Triglycerides mg/dl | 35.14 | 4.26 | 5 | 46.76 | 11.39 | 5 | 45.54 | 4.70 | 5 |
| Urea mg/dl | 56.74 | 3.94 | 5 | 52.90 | 4.48 | 5 | 54.26 | 4.90 | 5 |

TABLE 8

Organs weight data (male and female rats). Repeated dose dermal toxicity test (21 days) on rats of topical compositions comprising purified and lyophilized supernatant of *C. histolyticum* culture (ATCC 21000) using an animal product-free culture medium comprising soy peptone (30 g/L), yeast extract (30 g/L), cysteine hydrochloride (0.625 g/L) and arginine hydrochloride (3.75 g/L). Control composition: only with excipients.

| | Groups - males | | | | | | | | |
|---|---|---|---|---|---|---|---|---|---|
| | 0.2 U/g | | | 0.6 U/g | | | 1.8 U/g | | |
| | MEAN | S.D. | n | MEAN | S.D. | n | MEAN | S.D. | n |
| Liver Absolute (g) | 9.4932 | 0.7372 | 5 | 9.2295 | 0.7889 | 5 | 9.7103 | 0.9560 | 5 |
| Liver Relative | 0.0338 | 0.0022 | 5 | 0.0338 | 0.0023 | 5 | 0.0333 | 0.0010 | 5 |
| Kidneys Absolute (g) | 2.4209 | 0.0849 | 5 | 2.2266 | 0.1520 | 5 | 2.4551 | 0.2097 | 5 |
| Kidneys Relative | 0.0086 | 0.0005 | 5 | 0.0082 | 0.0004 | 5 | 0.0084 | 0.0003 | 5 |
| Adrenal Absolute (g) | 0.1014 | 0.0078 | 5 | 0.0968 | 0.0144 | 5 | 0.1026 | 0.0108 | 5 |
| Adrenal Relative | 0.0004 | 0.0000 | 5 | 0.0004 | 0.0001 | 5 | 0.0004 | 0.0000 | 5 |
| Testicles Absolute. | 3.5685 | 0.2740 | 5 | 3.1856 | 0.3267 | 5 | 3.4118 | 0.0909 | 5 |
| Testicles Relative | 0.0127 | 0.0010 | 5 | 0.0116 | 0.0005 | 5 | 0.0118 | 0.0007 | 5 |
| Test-Systems (g) | 280.94 | 19.34 | 5 | 273.42 | 18.43 | 5 | 291.20 | 20.19 | 5 |

| | Groups - males | | | | | | | | |
|---|---|---|---|---|---|---|---|---|---|
| | Control | | | Satellite-Control | | | 1.8 U/g-Satellite | | |
| | MEAN | S.D. | n | MEAN | S.D. | n | MEAN | S.D. | n |
| Liver Absolute (g) | 9.0665 | 0.6492 | 5 | 10.4859 | 1.0222 | 5 | 11.7093 | 0.8423 | 5 |
| Liver Relative | 0.0325 | 0.0013 | 5 | 0.0323 | 0.0024 | 5 | 0.0346 | 0.0010 | 5 |
| Kidneys Absolute (g) | 2.2151 | 0.0912 | 5 | 2.6912 | 0.2611 | 5 | 2.6810 | 0.2522 | 5 |
| Kidneys Relative | 0.0080 | 0.0004 | 5 | 0.0083 | 0.0006 | 5 | 0.0079 | 0.0009 | 5 |

TABLE 8-continued

Organs weight data (male and female rats). Repeated dose dermal toxicity test (21 days) on rats of topical compositions comprising purified and lyophilized supernatant of *C. histolyticum* culture (ATCC 21000) using an animal product-free culture medium comprising soy peptone (30 g/L), yeast extract (30 g/L), cysteine hydrochloride (0.625 g/L) and arginine hydrochloride (3.75 g/L). Control composition: only with excipients.

|  | MEAN | S.D. | n | MEAN | S.D. | n | MEAN | S.D. | n |
|---|---|---|---|---|---|---|---|---|---|
| Adrenal Absolute (g) | 0.0919 | 0.0124 | 5 | 0.1212 | 0.0120 | 5 | 0.1168 | 0.0085 | 5 |
| Adrenal Relative | 0.0003 | 0.0000 | 5 | 0.0004 | 0.0000 | 5 | 0.0003 | 0.0000 | 5 |
| Testicles Absolute. | 3.1967 | 0.1139 | 5 | 3.5597 | 0.2256 | 5 | 3.5676 | 0.3147 | 5 |
| Testicles Relative | 0.0115 | 0.0007 | 5 | 0.0110 | 0.0007 | 5 | 0.0106 | 0.0011 | 5 |
| Test-Systems (g) | 278.96 | 16.01 | 5 | 324.26 | 9.24 | 5 | 338.34 | 17.92 | 5 |

| | Groups - females | | | | | | | | |
|---|---|---|---|---|---|---|---|---|---|
| | 0.2 U/g | | | 0.6 U/g | | | 1.8 U/g | | |
| | MEAN | S.D. | n | MEAN | S.D. | n | MEAN | S.D. | n |
| Liver Absolute (g) | 8.5915 | 0.4047 | 5 | 7.3860 | 0.8336 | 5 | 9.0608 | 0.1947 | 5 |
| Liver Relative | 0.0352 | 0.0017 | 5 | 0.0347 | 0.0028 | 5 | 0.0377 | 0.0015 | 5 |
| Kidneys Absolute (g) | 1.9906 | 0.1441 | 5 | 1.7287 | 0.1963 | 5 | 1.9488 | 0.0750 | 5 |
| Kidneys Relative | 0.0082 | 0.0009 | 5 | 0.0081 | 0.0007 | 5 | 0.0081 | 0.0003 | 5 |
| Adrenal Absolute (g) | 0.1230 | 0.0139 | 5 | 0.1155 | 0.0189 | 5 | 0.1180 | 0.0201 | 5 |
| Adrenal Relative | 0.0005 | 0.0001 | 5 | 0.0005 | 0.0001 | 5 | 0.0005 | 0.0001 | 5 |
| Test-systems (g) | 244.42 | 15.77 | 5 | 212.52 | 12.20 | 5 | 240.98 | 12.59 | 5 |

| | Groups - females | | | | | | | | |
|---|---|---|---|---|---|---|---|---|---|
| | Control | | | Satellite-Control | | | 1.8 U/g-Satellite | | |
| | MEAN | S.D. | n | MEAN | S.D. | n | MEAN | S.D. | n |
| Liver Absolute (g) | 7.4838 | 0.3414 | 5 | 7.8360 | 0.3740 | 5 | 7.7555 | 0.5574 | 5 |
| Liver Relative | 0.0332 | 0.0007 | 5 | 0.0317 | 0.0010 | 5 | 0.0314 | 0.0018 | 5 |
| Kidneys Absolute (g) | 1.8299 | 0.0613 | 5 | 1.9183 | 0.1122 | 5 | 1.9155 | 0.1215 | 5 |
| Kidneys Relative | 0.0081 | 0.0005 | 5 | 0.0078 | 0.0005 | 5 | 0.0078 | 0.0005 | 5 |
| Adrenal Absolute (g) | 0.1008 | 0.0071 | 5 | 0.1257 | 0.0184 | 5 | 0.1211 | 0.0158 | 5 |
| Adrenal Relative | 0.0004 | 0.0000 | 5 | 0.0005 | 0.0001 | 5 | 0.0005 | 0.0001 | 5 |
| Test-systems (g) | 225.42 | 13.91 | 5 | 247.16 | 6.91 | 5 | 247.12 | 7.71 | 5 |

Example 9. Production of a Supernatant of *C. histolyticum* Liquid Culture (ATCC 21000 and T248 Strains) Comprising Collagenolytic and Gelatinolytic Proteases in Animal Product-Free Culture Medium—Bioreactor Culture The bioreactors cultures and the analytical methods were carried out as previously described in Example 5, using Medium 6 (comprising cysteine and arginine) as the culture medium of step 3.

FIG. 14 shows a comparative analysis of the collagenolytic and gelatinolytic activities (mU/mL) and optical density (OD 600 nm) of *Clostridium histolyticum* ATCC 21000 and T248 cultures. There is no significant difference (statistical analysis: Mann Whitney, p<0.05) between the collagenolytic and gelatinolytic activity of the supernatants of the culture of both *C. histolyticum* strains.

Example 10. Cytotoxicity Test of Collagenolytic and Gelatinolytic Proteases Obtained from *Clostridium histolyticum* (ATCC 21000 e T248) Liquid Culture Supernatant Using an Animal Product-Free Culture Medium The collagenolytic and gelatinolytic proteases were obtained according to Example 6 (lyophilize samples).

The cells used in the cytotoxicity test were a fibroblastic type, from a lineage established in V79 clone M-8 cultures from Chinese Hamster (*Cricetulus griseus*) lung. The fibroblasts were maintained in 25 cm² culture flasks (TPP, Techno Plastic Products AG, Trasadingen, Switzerland) until the confluence density was achieved. The culture was carried out in DMEM culture medium supplemented with 10% of bovine calf serum (Nutricell), 100 UI/mL of penicillin and 100 μg/mL of streptomycin sulfate (Nutricell), in a 37° C. incubator with humidified atmosphere with 5% $CO_2$ (Melo et al., 2000, 2001).

The cytotoxicity test was performed in 96 well plates (IWAKI, Asahi Techno Glass, Co., Funabasi, Japan), with $3\times10^4$ cells/mL in each well, followed by a 48 hour incubation time at 37° C. The initial cellular viability was verified through a Trypan Blue exclusion test. After the incubation of 48 hours the medium was replaced by a supplemented DMEM medium with different concentrations (up to 1 mg/mL) of the lyophilized samples described below:

| Sample | Origin | Strains |
|---|---|---|
| 1 | acquired from third-parties | — |
| 2 | acquired from third-parties | — |
| 3 | Obtained according to the present invention (Example 6) | ATCC 21000 |
| 4 | Obtained according to the present invention (Example 6) | ATCC 21000 |
| 5 | Obtained according to the present invention (Example 6) | T248 |

After 24 hours of treatment, the cultures were processed according to specific test protocols in order to determine acid nucleic content, neutral red incorporation (NR) and MTT reduction (MTT).

The collagenolytic and gelatinolytic proteases obtained from *C. histolyticum* cultures according to the present invention did not demonstrate cytotoxicity, as observed in the results presented in Table 9.

TABLE 9

Cytotoxicity test of collagenolytic and gelatinolytic proteases obtained from *C. histolyticum* cultures supernatants - ATCC 21000 e T248 - produced according to the present invention and from the raw material acquired from third parties.

| Sample | Activity (U/g) | IC50 (mg/mL) | | | IC50 (U/mL) | | |
|---|---|---|---|---|---|---|---|
| | | MTT | VN | nucleic acids | MIT | VN | nucleic acids |
| 1 | 2214.00 | 0.35 | 0.35 | 0.35 | 0.69 | 0.69 | 0.648 |
| 2 | 2090.00 | 0.33 | 0.31 | 0.31 | 0.69 | 0.69 | 0.648 |
| 3 | 2429.00 | * | 0.90 | 0.90 | 2.43 | 2.43 | 2.186 |
| 4 | 3073.00 | * | * | * | 3.07 | 3.07 | 3.073 |
| 5 | 3646.00 | 0.20 | 0.20 | 0.20 | 0.73 | 0.73 | 0.729 |

The invention claimed is:

1. An animal product-free culture medium for *Clostridium histolyticum* comprising water, vegetable peptone at a concentration range from 0.5% to 5% w/v, yeast extract at a concentration range from 0.5% to 5% w/v, cysteine hydrochloride at a concentration range from 0.01% to 0.1% w/v, and arginine hydrochloride at a concentration range from 0.1% to 1%; and a *Clostridium histolyticum* bacterium.

2. The culture medium according to claim 1, wherein the vegetable peptone is selected from the group consisting of soy, cotton, wheat, sunflower, rice, peanuts, fava bean, peas, potato, corn and mixtures thereof.

3. The culture medium according to claim 1, wherein the vegetable peptone is at a concentration of 3% w/v, yeast extract is at a concentration of 3% w/v, cysteine hydrochloride is at a concentration of 0.0625% w/v and arginine hydrochloride is at a concentration of 0.375% w/v.

4. The culture medium according to claim 1, wherein the vegetable peptone is soy peptone.

5. An animal product-free culture medium for *Clostridium histolyticum* comprising water, vegetable peptone at a concentration range from 0.5% to 5% w/v, yeast extract at a concentration range from 0.5% to 5% w/v, cysteine hydrochloride at a concentration range from 0.01% to 0.1% w/v, and arginine hydrochloride at a concentration range from 0.1% to 1%; that is liquid and sterile.

6. A process for producing a supernatant of *Clostridium histolyticum* liquid culture comprising one or more collagenolytic and gelatinolytic proteases comprising the following steps:
   a) providing a sterile animal product-free culture medium;
   b) culturing *Clostridium histolyticum* stock culture in the culture medium of step (a), under anaerobic conditions at about 37° C. before reaching the stationary growth phase in order to obtain an inoculum;
   c) providing a sterile animal product-free culture medium comprising vegetable peptone at a concentration range from 0.5% to 5% w/v, yeast extract at a concentration range from 0.5% to 5% w/v, cysteine hydrochloride at a concentration range from 0.01% to 0.1% w/v, and arginine hydrochloride at a concentration range from 0.1% to 1%;
   d) adding to the culture medium of step (c) a volume of inoculum from step (b) equal to or lower than 10% of the final volume of the medium defined in (c);
   e) culturing the *C. histolyticum* obtained in (d) under anaerobic conditions at about 37° C. until the stationary growth phase;
   f) removing cellular debris and other particulate matter from the liquid phase of the culture from step (e), yielding a supernatant comprising one or more collagenolytic and gelatinolytic proteases.

7. The process according to claim 6, wherein the step (b) comprises at least the following steps: 1) culturing a stock culture in the culture medium from step (a) in a ratio of 0.1:1 v/v for about 16 hours in order to obtain a pre-inoculum; 2) adding to the pre-inoculum obtained in step (1) an amount of culture medium from step (a) equal to or higher than the double of the culture medium volume from step (1) and maintaining the culture for about 12 hours in order to obtain an inoculum.

8. The process according to claim 6, wherein the *C. histolyticum* culture during the step (e) comprises the addition of one or more agents to pH adjustment in sufficient amount to maintain the culture medium pH from 6.5 to 8.0 and wherein the step (f) is carried out through filtration, centrifugation or both.

9. The process according to claim 6, comprising one or more additional steps for the purification of one or more collagenolytic and gelatinolytic proteases from the supernatant obtained in step (f).

10. The process according to claim 6, wherein the animal product-free culture medium employed in step (a) comprises water, 0.5% to 5% w/v of vegetable peptone, 0.5% to 5% w/v of yeast extract, 0.01% to 0.1% w/v of cysteine hydrochloride, and pH ranging from 6.5 to 8.0.

11. The process according to claim 10, wherein the culture medium employed in step (a) comprises water, 3% w/v of vegetable peptone, 3% w/v of yeast extract, 0.0625% w/v of cysteine hydrochloride, and pH ranging from 6.5 to 8.0.

12. The process according to claim 6, wherein the vegetable peptone is soy peptone.

\* \* \* \* \*